US009359557B2

(12) United States Patent
Hamilton et al.

(10) Patent No.: US 9,359,557 B2
(45) Date of Patent: *Jun. 7, 2016

(54) PROCESS FOR PRODUCING VOLATILE ORGANIC COMPOUNDS FROM BIOMASS MATERIAL

(71) Applicant: SHELL OIL COMPANY, Houston, TX (US)

(72) Inventors: Phillip Guy Hamilton, Sugar Land, TX (US); Corey William Radtke, Katy, TX (US); Keith Michael Kreitman, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,882

(22) Filed: May 16, 2013

(65) Prior Publication Data

US 2013/0309735 A1    Nov. 21, 2013

Related U.S. Application Data

(60) Provisional application No. 61/648,109, filed on May 17, 2012, provisional application No. 61/786,844, filed on Mar. 15, 2013, provisional application No. 61/786,860, filed on Mar. 15, 2013.

(51) Int. Cl.

| | | |
|---|---|---|
| *C12P 7/06* | (2006.01) | |
| *C12P 7/08* | (2006.01) | |
| *C10G 1/00* | (2006.01) | |
| *C12P 7/00* | (2006.01) | |
| *C12P 5/00* | (2006.01) | |
| *C12F 3/10* | (2006.01) | |
| *C10G 3/00* | (2006.01) | |
| *C12P 7/10* | (2006.01) | |
| *C12P 5/02* | (2006.01) | |
| *C10G 1/02* | (2006.01) | |

(52) U.S. Cl.
CPC ... *C10G 1/002* (2013.01); *C10G 1/02* (2013.01); *C10G 3/46* (2013.01); *C10G 3/50* (2013.01); *C12F 3/10* (2013.01); *C12P 5/00* (2013.01); *C12P 5/02* (2013.01); *C12P 5/026* (2013.01); *C12P 7/00* (2013.01); *C12P 7/06* (2013.01); *C12P 7/10* (2013.01); *Y02E 50/16* (2013.01); *Y02E 50/17* (2013.01); *Y02E 50/343* (2013.01); *Y02P 30/20* (2015.11); *Y02T 50/678* (2013.01)

(58) Field of Classification Search
USPC .................................. 435/161, 163
IPC .................................. C12P 7/06,7/08
See application file for complete search history.

(56) References Cited

U.S. PATENT DOCUMENTS

| | | | |
|---|---|---|---|
| 3,549,319 | A | 12/1970 | Wilson |
| 4,503,079 | A | 3/1985 | King et al. |
| 5,536,325 | A | 7/1996 | Brink |
| 5,789,210 | A | 8/1998 | Ho et al. |
| 6,475,768 | B1 | 11/2002 | Otero et al. |
| 6,818,803 | B1 | 11/2004 | Austin-Phillips et al. |
| 7,285,179 | B2 | 10/2007 | Snekkenes et al. |
| 7,510,857 | B2 | 3/2009 | Brumm |
| 7,781,191 | B2 | 8/2010 | Dunson, Jr. et al. |
| 7,973,199 | B2 | 7/2011 | Masuda et al. |
| 8,480,765 | B2 | 7/2013 | Siskin et al. |
| 8,641,910 | B2 | 2/2014 | Wietgrefe |
| 8,658,407 | B2 | 2/2014 | Lyons et al. |
| 8,835,156 | B2 | 9/2014 | Bjornsson |
| 2003/0162271 | A1 | 8/2003 | Zhang et al. |
| 2006/0292264 | A1 | 12/2006 | Young et al. |
| 2008/0216391 | A1 | 9/2008 | Cortright et al. |
| 2009/0226571 | A1 | 9/2009 | Freyer et al. |
| 2009/0239279 | A1 | 9/2009 | Hall et al. |
| 2010/0236988 | A1 | 9/2010 | Gabrielov et al. |
| 2010/0248320 | A1 | 9/2010 | Lyons et al. |
| 2010/0249470 | A1 | 9/2010 | Schirmer et al. |
| 2011/0015445 | A1 | 1/2011 | Masuda et al. |
| 2011/0100359 | A1 | 5/2011 | North |

(Continued)

FOREIGN PATENT DOCUMENTS

| | | |
|---|---|---|
| AU | 2013262755 | 1/2015 |
| AU | 2013262757 | 1/2015 |

(Continued)

OTHER PUBLICATIONS

Anonymous. Guide to Agricultural PM10 Best Management Practices; (2008) pp. 1-29. downloaded from http://www.azda.gov/act/Best%20Management%20Practices%20Guide%20for%20web%20view%20reduce.pdf on Mar. 27, 2014.*
Morey et al. Superheated Steam Drying Technology in an Ethanol Production Process; 2010 ASABE Annual International Meeting, Jun. 20-23, 2010. pp. 1-11. downloaded from http://www.biomasschpethanol.umn.edu/August%202010%20updates/Superheated%20Steam%20Morey%209069.pdf on Mar. 27, 2014.*
M. Bahree, Forbes (2009) Sorghum for Ethanol downloaded from http://www.forbes.com/forbes/2009/0907/international-united-phosphorus-fuel-sorghum-for-ethanol.htm on Mar. 27, 2014.*
Morey, R. Project Title: Biomass Electricity Generation at Ethanol Plants-Achieving Maximum Impact; (2009), pp. 1-20 downloaded from http://www.xcelenergy.com/staticfiles/xe/Corporate/Renewable%20Energy520Grants/EthanolBEMGaEP-M4.pdf on Apr. 22, 2015.*
Kosaric et al. Ethanol; Ullmann's Encyclopedia of Industrial Chemistry (2011) pp. 333-403.*

(Continued)

*Primary Examiner* — Kagnew H Gebreyesus
*Assistant Examiner* — Paul Martin

(57) ABSTRACT

Embodiments of the present invention provide for efficient and economical production and recovery of ethanol or other volatile organic compounds, such as acetic acid, from solid biomass material, particularly on a larger scale, such as on the commercialization or industrial scale. According to one aspect of the invention, the method comprises (a) generating at least about 10 tons of prepared biomass material by adding a microbe, optionally an acid, and optionally, an enzyme to a solid biomass; (b) storing the prepared biomass material for at least about 24 hours in a storage facility to allow production of at least one volatile organic compound from at least a portion of the sugar in the solid biomass; and (c) capturing the at least one volatile organic compound by using a solventless recovery system.

35 Claims, 2 Drawing Sheets

(56) References Cited

U.S. PATENT DOCUMENTS

| | | |
|---|---|---|
| 2011/0108409 A1 | 5/2011 | Brown |
| 2011/0154721 A1 | 6/2011 | Chheda et al. |
| 2011/0154722 A1 | 6/2011 | Chheda et al. |
| 2011/0282115 A1 | 11/2011 | Chheda et al. |
| 2012/0317872 A1 | 12/2012 | Powell |
| 2013/0052709 A1 | 2/2013 | Wietgrefe et al. |
| 2013/0305598 A1 | 11/2013 | Hamilton et al. |

FOREIGN PATENT DOCUMENTS

| | | |
|---|---|---|
| CA | 2873303 | 11/2013 |
| CN | 1140556 | 1/1997 |
| CN | 101085995 | 12/2007 |
| CN | 101300359 | 11/2008 |
| CN | 101503713 | 8/2009 |
| CN | 101235391 | 8/2011 |
| CN | 102399826 | 4/2012 |
| CN | 102449156 | 5/2012 |
| GB | 2141316 | 12/1984 |
| GB | 2201413 | 9/1988 |
| JP | 2009136201 | 6/2009 |
| JP | 2009136202 | 6/2009 |
| JP | 2009209059 | 9/2009 |
| JP | 2009535038 | 10/2009 |
| JP | 2011182685 | 9/2011 |
| JP | 2012055302 | 3/2012 |
| WO | 9113099 | 9/1991 |
| WO | 9513362 | 5/1995 |
| WO | 9742307 | 11/1997 |
| WO | 9745430 | 12/1997 |
| WO | 9811235 | 3/1998 |
| WO | 2005093041 | 10/2005 |
| WO | 2006096130 | 9/2006 |
| WO | 2007028811 | 3/2007 |
| WO | 2007100897 | 9/2007 |
| WO | 2007127912 | 11/2007 |
| WO | 2007136762 | 11/2007 |
| WO | 2008119082 | 10/2008 |
| WO | 2009058276 | 5/2009 |
| WO | 2009109631 | 9/2009 |
| WO | 2010028206 | 3/2010 |
| WO | 2010065643 | 6/2010 |
| WO | 2010096510 | 8/2010 |
| WO | 2010107944 | 9/2010 |
| WO | 2011039635 | 4/2011 |
| WO | 2011057159 | 5/2011 |
| WO | 2011082000 | 7/2011 |
| WO | 2011143391 | 11/2011 |
| WO | 2011149956 | 12/2011 |
| WO | 2012145123 | 10/2012 |
| WO | 2013173560 | 11/2013 |
| WO | 2013173562 | 11/2013 |
| WO | 2013173563 | 11/2013 |
| WO | 2013173576 | 11/2013 |

OTHER PUBLICATIONS

Henk, L., et al.; "Solid State Production of Ethanol From Sorghum"; Applied Biochemistry and Biotechnology; vol. 57/58; pp. 489-501; 1996.

Webster, A., et al.; "Observations of the Harvesting, Transporting and Trial Crushing of Sweet Sorghum in a Sugar Mill"; Conference of the Australian Society of Sugar Can Technologist; Brisbane, Queensland Australia; May 2004.

Andrzejewski, et al; "Development of Commercially Viable Processing Technologies for Sweet Sorghum"; USDA-ARS-Southern Regional Research Center in New Orleans; Sweet Sorghum Ethanol Conference held Jan. 26, 2012.

Bellmer, D.; "The untapped Potential of Sweet Sorghum as a Bioenergy Feedstock"; Sweet Sorghum Ethanol Conference, Jan. 26, 2012.

Wu, et al.; "Features of Sweet Sorghum Juice and their Performance in Ethanol Fermentation"; Industrial Crops and Products 31; pp. 164-170; 2010.

Bennet, et al.; "Farm-gate Productions Costs of Sweet Sorgham as a Bioethanol Feedstock"; American Society of Agricultural and Biological Engineers; vol. 5(2); pp. 603-613; 2008.

Shen, F.; et al.; "Research on Solid-State Ethanol Fermentation Using Dry Sweet Sorghum Stalk particles with Active Dry Yeast"; Energy & Fuels; vol. 23; pp. 519-525; 2009.

Iman et al; Ethanol Fermentation from Sweet Sorghum Juice; ASABE Annual International Meeting; Pittsburg PA; pp. 1-8; 2010.

Lingle et al; "Post-harvest Changes in Sweet Sorghum 1: Brix and Sugars"; Bioenerg. Res.; vol. 5; pp. 158-167; 2012.

Radtke, et al. "Milestone Completion Report"; Idaho National Laboratory; pp. 1-30; Sep. 29, 2007.

Noah, et al.; "Extraction on Ensiled Sweet Sorghum with a Continuous Countercurrent Diffuser", American Society of Agricultural Engineers; vol. 32, No. 4; pp. 1419-1425; Jul.-Aug. 1989.

Schmidt, et al.; "Preservation of Sugar Content in Ensiled Sweet Sorghum"; Bioresource Technology; vol. 60; pp. 9-13; 1997.

Bellmer, D., et al.; "The Untapped Potential of Sweet Sorghum as a Bioenergy Feedstock"; Biofuels; vol. 1(4); pp. 563-573; 2010.

Radtke, et al., Crossover 2007 Bioenergy: From Fields to Wheels Presentation; pp. 1-22; Sep. 4, 2007.

International Search Report for PCT/US2013/041309 dated Sep. 5, 2013; 5 pages.

International Search Report for PCT/ US2013/041313 dated Sep. 2, 2013; 5 pages.

Morgan et al; Volatile constituents of grass and corn silage.I. Steam distillates; Journal of Dairy Science; vol. 45, No. 4; pp. 457-466; Apr. 22, 2001.

GEA Superheated Steam Dryer brochure. 4 pgs.

International Search Report—PCT/US2013/041306 dated Aug. 19, 2013; 5 pages.

International Search Report—PCT/US2013/041339 dated Oct. 28, 2013; 7 pages.

International Search Report—PCT/US2013/041327 dated Sep. 16, 2013; 4 pages.

Brooks, et al., "Bioconversion of Plant Biomass to Ethanol"; Sol. Energy Res. Inst., Biomass Energy Syst. Conf. Proc., 1979, 3rd Ed., pp. 275-280.

Bryan, W., "Solid-State Fermentation of Sugars in Sweet Sorghum"; Enzyme Microb. Technal., 1990, vol. 12, pp. 437-442.

Gupta, Rajan et al., "Liquid-Liquid Extraction Using the Composition-Induced Phase Separation Process", Ind. Eng. Chem. Res., 1996, vol. 35, pp. 2360-2368.

Hendriks & Zeeman (2009), Bioresource Technology, 2009, vol. 100, pp. 10-18.

Henk Linda L, et al., Solid-State Production of Ethanol from Sorghum, Applied Biochemistry and Biotechnology; Part A: Enzyme Engineering and Biotechnology, Humana Press Inc., NY, vol. 57-58, No. 1, Mar. 1, 1996, pp. 489-501.

International Search Report for Ref. No. TH4245-PCT dated Sep. 5, 2013, Application No. PCT/US2013/041309 filed May 16, 2013.

Li, N. et al., "Renewable Gasoline from Aqueous Phase Hydrodeoxygenation of Aqueous Sugar Solutions Prepared by Hydrolysis of Maple Wood", The Royal Society of Chemistry, 2011, Green Chemistry, vol. 13, No. 1, pp. 91-101.

Radtke, et al. "Milestone Completion Report"; Idaho National Laboratory; pp. 1-30, Sep. 29, 2007.

Renon Henri et al., "Local Compositions in Thermodynamic Excess Functions for Liquid Mixtures", AIChE Journal, vol. 14, No. 1, pp. 135-144, Jan. 1968.

Sagehashi M. et al., Superheated Steam Pyrolysis of Biomass Elemental Components and Sugi (Japanese cedar) for Fuels and Chemicals, Bioresource Technology, Elsevier BV, GB, vol. 97, No. 11, Jul. 1, 2006, pp. 1272-1283.

Zhu, J.Y., et al., "Woody Biomass Pretreatment for Cellulosic Ethanol Production: Technology and Energy Consumption Evaluation", Bioresource Technology, vol. 101 (2010) pp. 4992-5002.

International Search Report dated Sep. 2, 2013, Application No. PCT/US2013/041313 filed May 16, 2013.

(56) References Cited

OTHER PUBLICATIONS

Bahrin, E. K. et al., "Physicochemical Property Changes and Enzymatic Hydrolysis Enhancement of Oil Palm Empty Fruit Bunches Treated with Superheated Steam", Bioresources, 2012, vol. 7, pp. 1784-1801.

Guide to Agricultural PM10 Best Management Practices, Governor's Agricultural Best Management Practices Committee, 2nd Ed., 2008, pp. 1-29.

Zhao, X. et al, "Organosolve Pretreatment of Lignocellulosic Biomass for Enzymatic Hydrolysis", Applied Microbioligy & Biotechnology, vol. 82, pp. 815-827, 2009.

* cited by examiner

PROCESS FOR PRODUCING VOLATILE ORGANIC COMPOUNDS FROM BIOMASS MATERIAL

REFERENCE TO RELATED APPLICATIONS

The present application claims priority to U.S. Provisional Application No. 61/648,109, filed on May 17, 2012, U.S. Provisional Application No. 61/786,844, filed on Mar. 15, 2013, and U.S. Provisional Application No. 61/786,860, filed on Mar. 15, 2013, the disclosures of which are incorporated by reference herein in their entirety.

FIELD OF THE INVENTION

Embodiments of this invention relate generally to a process for producing volatile organic compounds, such as ethanol, from biomass material, and more particularly to fermentation and recovery of such volatile organic compounds from biomass material.

BACKGROUND OF THE INVENTION

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of any prior art.

As the world's petroleum supplies continue to diminish there is a growing need for alternative materials that can be substituted for various petroleum products, particularly transportation fuels. In the U.S., environmental regulations, such as the Clean Air Act of 1990, provide incentives for the use of oxygenated fuels in automobiles. Ethanol or methyl tertiary butyl ether (MTBE) boosts the oxygen content in gasoline and reduces carbon monoxide emissions. One principal advantage for the use of ethanol is that the fuel is produced from renewable resources. Atmospheric levels of carbon dioxide, a greenhouse gas, can be decreased by replacing fossil fuels with renewable fuels.

Currently much effort is underway to produce bioethanol that is derived from renewable biomass materials, such as corn, sugar crops, energy crops, and solid waste. Conventional ethanol production from corn typically competes with valuable food resources, which can be further amplified by increasingly more severe climate conditions, such as droughts and floods, which negatively impact the amount of crop harvested every year. The competition from conventional ethanol production can drive up food prices. While other crops have served as the biomass material for ethanol production, they usually are not suitable for global implementations due to the climate requirements of such crops. For instance, ethanol can also be efficiently produced from sugar cane, but only in certain areas of the world, such as Brazil, that have a climate that can support near-year-round harvest.

While other approaches of producing ethanol that do not use corn are available, they are still lacking. For example, Henk and Linden at Colorado State University investigated solid-state production of ethanol from *sorghum* (see *Solid State Production of Ethanol from Sorghum*, Linda L. Henk and James C. Linden, Applied Biochemistry and Biotechnology, Vol. 57/58, 1996, pp. 489-501). They noted for sweet *sorghum* to be used successfully for ethanol production, three issues needed to be addressed:

Carbohydrate storage;
Accessibility of the ligno-cellulosic fraction to enzymatic hydrolysis of hemicellulose and cellulose; and
A more economical means of recovering the ethanol from the sweet *sorghum*.

In their process, they pointed out that seasonal availability and storability of sweet *sorghum* are important factors in the use of this renewable biomass. Sugar extraction and storability are two serious problems that have limited the use of sweet *sorghum* as a substrate for ethanol production. Traditional applications envision using juice containing about 10-15% sugar that has been extracted or pressed from the sweet *sorghum* pulp. The juice is then either fermented directly to alcohol or evaporated to molasses for storage. Direct fermentation of the juice to ethanol is a seasonal process, accomplished for only a short time after harvest. This presents challenges to scaling up solid state fermentation from an experimental stage to a larger practical stage, such as industrial scale. For example, the short harvesting window requires a substantial capital investment of storage space and recovery facilities to process the peak amount for a short period time while the space and equipment would sit dormant or be underutilized for the down time.

Henk and Linden's strategy to some of the problems of making sweet *sorghum* to ethanol was to investigate using wet stored solid state fermentation integrated into an economical method for long-term storage of ethanol in sweet *sorghum*. While Henk and Linden did show some improvements in the overall process, there are still a number of shortcomings, including the amount of ethanol they were able to produce. Such proposed systems tend to make bioethanol production even more expensive by typically requiring expensive equipment that needs costly maintenance. Also, Henk and Linden showed feasibility of solid state fermentation of *sorghum* on an experimental scale but did not provide details for a scale up operation.

For instance, Henk and Linden did not provide any means to economically recover the ethanol and other volatile organic compounds from the biomass solid material. Henk and Linden and others have not addressed the obstacles that render ethanol production from solid-state fermentation of *sorghum* economically feasible when it is operated on a larger scale, particularly an industrial scale.

Others have also recognized challenges to economically recover the ethanol and other volatile organic compounds from the biomass solid material. For instance, Webster et al. reported that using a forage harvester for sweet *sorghum* results in rapid juice deterioration and therefore not an attractive solution for bringing in sweet *sorghum* to sugar mills (see *Observations of the Harvesting, Transporting and Trial Crushing of Sweet Sorghum in a Sugar Mill*, Webster, A., et al, 2004 Conference of the Australian Society of Sugar Cane Technologist, Brisbane, Queensland, Australia (May 2004)). Andrzejewski and Eggleston reported that challenges in making U.S. sweet *sorghum* to ethanol (or other uses) viable revolve around the storage of the juice because of the relatively narrow harvest window of sweet *sorghum* in the United States (see *Development of commercially viable processing technologies for sweet sorghum at USDA-ARS-Southern Regional Research Center in New Orleans*, Andrzejewski and Eggleston, Sweet *Sorghum* Ethanol Conference, Jan. 26, 2012). In particular, the challenges include (i) clarification (removal of suspended and turbid particles) of the raw juice to make it suitable for concentration and/or fermentation, (ii) stabilization of juice or partially concentrated juice for cost-effective seasonal use (liquid feedstock), and (iii) concentration of juice into syrup for storage, year-round supply, and efficient transport (liquid feedstock).

Bellmer sought to improve the process by optimizing conditions around removing the juice from the solids before processing (see *The untapped potential of Sweet Sorghum as a Bioenergy Feedstock*, Bellmer, D., Sweet *Sorghum* Ethanol Conference, Jan. 26, 2012). Wu et al. recognized the technical challenges of using sweet *sorghum* for biofuels, including a short harvest period for highest sugar content, and fast sugar degradation during storage (see *Features of sweet sorghum juice and their performance in ethanol fermentation*, X. Wu et al., Industrial Crops and Products 31: 164-170, 2010). In particular, the study showed that as much as 20% of the fermentable sugars can be lost in 3 days. Bennet and Annex noted the limitations of using *sorghum* for ethanol production involving material transport cost and storability (see *Farm-gate productions costs of sweet sorghum as a bioethanol feedstock*, Transactions of the American Society of Agricultural and Biological Engineers, Vol. 51(2):603-613, 2008). While Bennet and Annex were aware of direct production of ethanol in ensilage inoculated with yeast, they concluded that such direct production method was impractical because of issues related to separating ethanol from silage, ensilage storage losses (up to 40% in bunker style silos), and the possible use of silage as an alternative fermentation feedstock have yet to be examined for industrial-scale applications.

Shen and Liu sought to address the long-time and effective storage of fresh stalk or juice by first dried the sweet *sorghum* in order to preserve the sugars, then plan to use the material year-round for ethanol production, thereby adding costs of material handling for drying, spreading the wet *sorghum* for drying, as well as adding restrictions to the process by requiring adequate weather conditions to achieve proper drying (see *Research on Solid-State Ethanol Fermentation Using Dry Sweet Sorghum Stalk Particles with Active Dry Yeast*, Shen, Fei and Liu, R., Energy & Fuels, 2009, Vol. 23, pgs. 519-525). Imam and Capareda sought to process the juice before fermentation and to increase the fermentation rates using a variety of options such as autoclave (heat treat), freeze, and to increase the sugar concentration (see *Ethanol Fermentation from Sweet Sorghum Juice*, Imam, T. and Capareda, S., ASABE, 2010 ASABE Annual International Meeting, Pittsburge, Pa. (June 2010)).

Bellmer, Huhnke, and Godsey noted challenges to using *sorghum* in ethanol production as: (i) storability of carbohydrates in sweet *sorghum*, (ii) quick sugar/carbohydrate degradation in-stalk after harvest, (iii) short shelf life of expressed juice, (iv) syrup production (dewatering) too costly (see *The untapped potential of sweet sorghum as a bioenergy feedstock*, Bellmer, D., Huhnke, R., and Godsey, C., Biofuels 1(4) 563-573, 2010). They used a solid phase fermenter, which are metallic containers including rotary drums and screw augers, which require expensive equipment. Further, use of a solid phase fermenter is also subject to the harvest window of the crop, e.g., sweet *sorghum*. Likewise, Noah and Linden noted storability and inefficient sugar extraction as the two major drawbacks to sweet *sorghum* use for fuels and chemicals.

In summary, obstacles in using *sorghum* and other plants containing fermentable sugars include the fact that they are only seasonally available and storage is costly, which make it challenging to use infrastructure efficiently and to schedule labor; sugar extraction and storability are two critical obstacles because conversion must be started immediately after harvest to avoid spoilage.

Thus, there is a need for a process to produce ethanol and other volatile organic compounds on a large scale from biomass material that addresses at least these obstacles, such as preferably not competing with the world's food source.

SUMMARY

Embodiments of the present invention provide a number of advantages over conventional processes. Embodiments of the invention allow for economical production of ethanol and other volatile organic compounds from plants that contain fermentable sugar by addressing the challenges, some of which noted above, such as needs of decentralized plants, short harvest windows, quick degradation of sugars, and large investment in equipment.

In certain embodiments, fermentation may be achieved by storing the prepared biomass material in one or more piles, thereby reducing or eliminating the need for expensive equipment as compared to the prior art fermentation process which generally requires significant capital investment. Embodiments of the invention allow for fermentation in conjunction with product storage where prior art fermentation of fermentable sugar crops often requires just-in-time harvesting to avoid spoilage, which makes the prior art operation time sensitive.

Embodiments of the invention allow for the recovery facility to run continuously year-round in a controlled manner independent of the harvest window, thereby broadening the geological locations available to place a recovery facility, including areas with a relatively short harvest window. For example, sugar cane ethanol plants in Brazil typically operate about nine months a year because that is the harvest window for sugar cane in Brazil. In the U.S., the same plant could only operate about three to five months per year because of the requirement for just in time harvest coupled with the short time of crop availability. Embodiments of the present invention eliminate or minimize the need for just-in-time harvesting allowing for year-round ethanol production regardless of the harvest window of the sugar crop.

Embodiments of the invention provide control over the period of fermentation and storage where there is minimal degradation of the volatile organic compounds for up to 700 days, thereby allowing for a short harvest window where the crop is closest to its peak sugar potential and field yield. This allows for harvesting at the optimal condition rather than conventional processes that may need to compromise the level of sugar production and field yield to obtain a longer harvesting window.

Further, embodiments of the invention allow for large scale production of ethanol or other volatile organic compounds, including recovery of sufficient amounts for commercialization or other industrial applications.

In a particular embodiment, there is provided a method for producing at least one volatile organic compound comprising: generating at least about 10 tons of prepared biomass material comprising at least one additive added to a solid biomass comprising a sugar, wherein said at least one additive comprise a microbe, and optionally, an acid and/or an enzyme; storing the prepared biomass material for at least about 24 hours in a storage facility to allow for the production of at least one volatile organic compound from at least a portion of the sugar; and capturing the at least one volatile organic compound by feeding the stored biomass material to a solventless recovery system to separate the stored biomass material into at least a gas component comprising the at least one volatile organic compound and a solid component.

In one embodiment, the capturing step comprises: introducing the prepared biomass material to an enclosed compartment of a solventless recovery system, wherein the prepared biomass material contains one or more volatile organic compounds; contacting the prepared biomass material with a superheated vapor stream in the enclosed compartment to vaporize at least a portion of an initial liquid content in the prepared biomass material, said superheated vapor stream comprising at least one volatile organic compound; separating a gas component and a solid component from the prepared biomass material, said gas component comprising at least one volatile organic compound; and retaining at least a portion of the gas component for use as part of the superheated vapor stream.

In another embodiment, there is provided a method for producing a storable wet biomass containing volatile organic compounds, said method comprising: adding at least one additive to at least about 10 tons of a solid biomass to generate a prepared biomass material, said solid biomass comprising a sugar-producing plant, wherein said at least one additive comprise a microbe, and optionally, an acid and/or an enzyme; and allowing conversion of at least a portion of the sugar in the prepared biomass material into a volatile organic compound; wherein the biomass material is capable of being stored for about 700 days without significant degradation of the volatile organic compound.

In addition to the features described above, embodiments of the invention allow for economical production of alternative fuels, such as ethanol and other volatile organic compounds, from plants that contain fermentable sugar by addressing challenges, such as costs of storage and transportation, short harvest windows, quick degradation of sugars, and large investment in equipment. Aspects of the embodiments described herein are applicable to any biomass material, such as plants containing fermentable sugars. The features of embodiments of the present invention allow for economical use of various plants to produce alternative fuels and chemicals and are not limited to *sorghum* and other plants that suffer similar challenges. Such challenging crops are highlighted herein because other methods and systems have not been able to economically use these challenging crops to produce fuels and chemicals. As such, the specific mention of *sorghum* is not intended to be limiting, but rather illustrates one particular application of embodiments of the invention.

Other features and advantages of embodiments of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These drawings illustrate certain aspects of some of the embodiments of the invention, and should not be used to limit or define the invention.

DETAILED DESCRIPTION OF PREFERRED EMBODIMENTS

Figure 1:
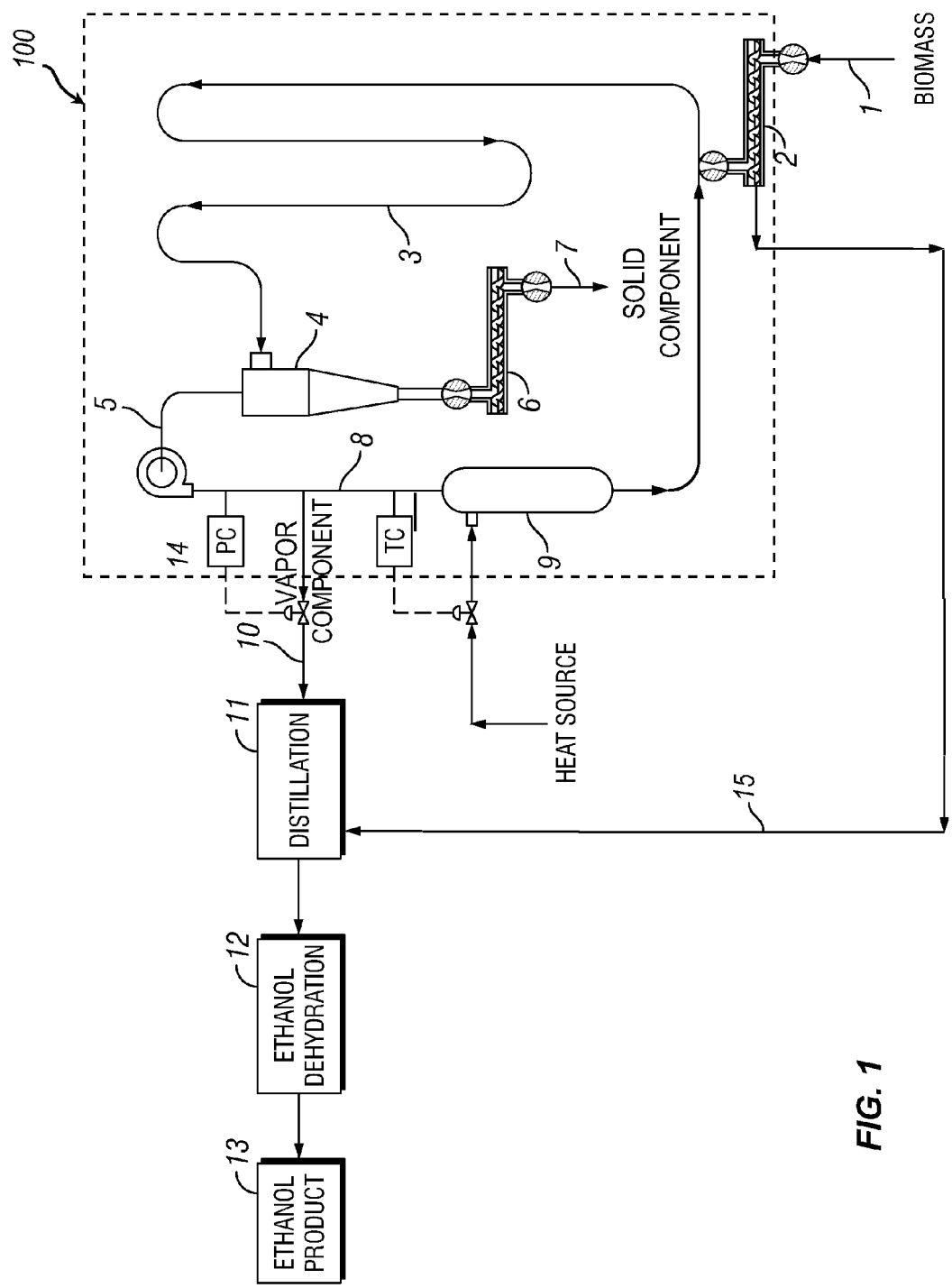
FIG. 1 is a diagram of one embodiment to process biomass material according to certain aspects of the present invention.

Embodiments of the present invention provide for efficient and economical production and recovery of ethanol or other volatile organic compounds, such as acetic acid, from solid biomass material, particularly on a larger scale, such as on the commercialization or industrial scale. According to one aspect of the invention, the method comprises (a) generating at least about 10 tons of prepared biomass material by adding a microbe, optionally an acid, and optionally, an enzyme to a solid biomass; (b) storing the prepared biomass material for at least about 24 hours in a storage facility to allow production of at least one volatile organic compound from at least a portion of the sugar in the solid biomass; and (c) capturing the at least one volatile organic compound by using a solventless recovery system.

As used herein, the term "solid biomass" or "biomass" refers at least to biological matter from living, or recently living organisms. Solid biomass includes plant or animal matter that can be converted into fibers or other industrial chemicals, including biofuels. Solid biomass can be derived from numerous types of plants or trees, including miscanthus, switchgrass, hemp, corn, tropical poplar, willow, *sorghum*, sugarcane, sugar beet, and any energy cane, and a variety of tree species, ranging from eucalyptus to oil palm (palm oil). In one embodiment, the solid biomass comprises at least one fermentable sugar-producing plant. The solid biomass can comprise two or more different plant types, including fermentable sugar-producing plant. The different plant types can have the same or different harvest season. In a preferred embodiment not intended to limit the scope of the invention, *sorghum* is selected, due to its high-yield on less productive lands and high sugar content.

The term "fermentable sugar" refers to oligosaccharides and monosaccharides that can be used as a carbon source (e.g., pentoses and hexoses) by a microorganism to produce an organic product such as alcohols, organic acids, esters, and aldehydes, under anaerobic and/or aerobic conditions. Such production of an organic product can be referred to generally as fermentation. The at least one fermentable sugar-producing plant contains fermentable sugars dissolved in the water phase of the plant material at one point in time during its growth cycle. Non-limiting examples of fermentable sugar-producing plants include *sorghum*, sugarcane, sugar beet, and energy cane. In particular, sugarcane, energy cane, and *sorghum* typically contain from about 5% to about 25% soluble sugar w/w in the water phase and have moisture content between about 60% and about 80% on a wet basis when they are near or at their maximum potential fermentable sugar production (e.g., maximum fermentable sugar concentration).

The term "wet basis" refers at least to the mass percentage that includes water as part of the mass. In a preferred embodiment, the sugar producing plant is *sorghum*. Any species or variety of the genus *sorghum* that provides for the microbial conversion of carbohydrates to volatile organic compounds (VOCs) can be used. For embodiments using *sorghum*, the plant provides certain benefits, including being water-efficient, as well as drought and heat-tolerant. These properties make the crop suitable for many locations, including various regions across the earth, such as China, Africa, Australia, and in the US, such as portions of the High Plains, the West, and across the South. Texas.

In embodiments using *sorghum*, the *sorghum* can include any variety or combination of varieties that may be harvested with higher concentrations of fermentable sugar. Certain varieties of *sorghum* with preferred properties are sometimes referred to as "sweet *sorghum*." The *sorghum* can include a variety that may or may not contain enough moisture to support the juicing process in a sugar cane mill operation. In a preferred embodiment, the solid biomass includes a Sugar T

*sorghum* variety commercially produced by Advanta and/or a male parent of Sugar T, which is also a commercially available product of Advanta. In a preferred embodiment, the crop used has from about 5 to about 25 brix, preferably from about 10 to about 20 brix, and more preferably from about 12 to about 18 brix. The term "brix" herein refers at least to the content of glucose, fructose, and sucrose in an aqueous solution where one degree brix is 1 gram of glucose, fructose, and/or sucrose in 100 grams of solution and represents the strength of the solution as percentage by weight (% w/w). In another preferred embodiment, the moisture content of the crop used is from about 50% to 80%, preferably at least 60%.

In one embodiment, the crop is a male parent of Sugar T with a brix value of about 18 and a moisture content of about 67%. In another embodiment, the crop is Sugar T with a brix value of about 12 at a moisture content of about 73%. In these particular embodiments, the brix and moisture content values were determined by handheld refractometer.

After at least one additive (a microbe, optionally, an acid and/or enzyme) is added to the solid biomass, it becomes prepared biomass material where the at least one additive facilitates the conversion of fermentable sugar into a VOC (such as ethanol). As noted above and further described below, the prepared biomass material can be stored for a certain period of time to allow more VOCs to be generated by the conversion process. At least one volatile organic compound is then recovered from the prepared biomass material. Volatile organic compounds are known to those skilled in the art. The U.S. EPA provides descriptions volatile organic compounds (VOC), one of which is any compound of carbon, excluding carbon monoxide, carbon dioxide, carbonic acid, metallic carbides or carbonates, and ammonium carbonate, which participates in atmospheric photochemical reactions, except those designated by EPA as having negligible photochemical reactivity (see http://www.epa.gov/iaq/voc2.html#definition). Another description of volatile organic compounds, or VOCs, is any organic chemical compound whose composition makes it possible for them to evaporate under normal indoor atmospheric conditions of temperature and pressure. This is the general definition of VOCs that is used in the scientific literature, and is consistent with the definition used for indoor air quality. Normal indoor atmospheric conditions of temperature and pressure refer to the range of conditions usually found in buildings occupied by people, and thus can vary depending on the type of building and its geographic location. One exemplary normal indoor atmospheric condition is provided by the International Union of Pure and Applied Chemistry (IUPAC) and the National Institute of Standards and Technology (NIST). IUPAC's standard is a temperature of 0° C. (273, 15 K, 32° F.) and an absolute pressure of 100 kPa (14.504 psi), and NIST's definition is a temperature of 20° C. (293, 15 K, 68° F.) and an absolute pressure of 101.325 kPa (14.696 psi).

Since the volatility of a compound is generally higher the lower its boiling point temperature, the volatility of organic compounds are sometimes defined and classified by their boiling points. Accordingly, a VOC can be described by its boiling point. A VOC is any organic compound having a boiling point range of about 50 degrees C. to 260 degrees C. measured at a standard atmospheric pressure of about 101.3 kPa. Many volatile organic compounds that can be recovered and/or further processed from VOCs recovered from embodiments of the present invention have applications in the perfume and flavoring industries. Examples of such compounds may be esters, ketones, alcohols, aldehydes, hydrocarbons and terpenes. The following Table 1 further provides non-limiting examples of volatile organic compounds that may be recovered and/or further processed from VOCs recovered from the prepared biomass material.

TABLE 1

| | | | |
|---|---|---|---|
| Methanol | Ethyl acetate | Acetaldehyde | Diacetyl |
| 2,3-pentanedione | Malic acid | Pyruvic acid | Succinic acid |
| Butyric acid | Formic acid | Acetic acid | Propionic acid |
| Isobutyric acid | Valeric acid | Isovaleric acid | 2-methylbutyric acid |
| Hexanoic acid | Heptanoic acid | Octanoic acid | |
| Decanoic acid | Propanol | Isopropanol | Nonanoic acid |
| Isobutanol | Isoamyl alcohol | Hexanol | Butanol |
| Tryptoptanol | Phenethyl alcohol | 2,3-butanediol | Tyrosol |
| Fumaric acid | Ethanol | Amyl alcohol | Glycerol |
| 1-propanol | 2-butanol | Methyl acetate | 1,2-propanol |
| Propyl acetate | Ethyl lactate | Propyl lactate | Ethyl acetate |
| Ethyl formate | n-propyl alcohol | 2-methyl-1-propanol | Acetone |
| 2,3-methyl-1-butanol | 3-buten-2-ol | | 2-propen-1-ol |

Ethanol is a preferred volatile organic compound. As such, many examples specifically mention ethanol. This specific mention, however, is not intended to limit the invention. It should be understood that aspects of the invention also equally apply to other volatile organic compounds. Another preferred volatile organic compound is acetic acid.

Embodiments of the present invention provide for the long term storage of solid biomass material without significant degradation to the volatile organic compounds contained in the prepared biomass material, and they provide for sugar preservation to allow for continued generation of VOCs. As used in this context, "significant" refers at least to within the margin of error when measuring the amount or concentration of the volatile organic compounds in the prepared biomass material. In one embodiment, the margin of error is about 0.5%.

Accordingly, embodiments of the present invention allow for continuous production VOCs without dependence on the length of the harvest, thereby eliminating or minimizing down time of a recovery plant in traditional just-in-time harvest and recovery processes. As such, embodiments of the present invention allow for harvest of the crop at its peak without compromises typically made to lengthen the harvest season, such as harvest slightly earlier and later than peak time. That is, embodiments of the invention allow for harvest at high field yields and high sugar concentrations, such as when the selected crop has reached its peak sugar concentration or amount of fermentable sugars that can be converted into a volatile organic compound, even if this results in a shorter harvest period. In one embodiment, the solid biomass is harvested or prepared when it is at about 80%, about 85%, about 90%, about 95%, or about 100% of its maximum potential fermentable sugar concentration. As such, embodiments of the present invention, particularly the recovery phase, can be operated continuously year-round without time pressure from fear of spoilage of the solid biomass and VOCs contained therein. While embodiments of the present invention allow for harvest of the solid biomass near or at its maximum sugar production potential, the solid biomass material can be harvested at any point when it is deemed to contain a suitable amount of sugar. Further, the harvest window varies depending on the type of crop and the geographical location. For example, the harvest window for *sorghum* in North America can range from about 1 to 7 months. However, in Brazil and other equatorial and near equatorial areas, the harvest window may be up to twelve months.

In embodiments using plants as the solid biomass, the solid biomass can be collected or harvested from the field using any suitable means known to those skilled in the art. In one embodiment, the solid biomass comprises a stalk component and a leaf component of the plant. In another embodiment, the solid biomass further comprises a grain component. In a preferred embodiment, the solid biomass is harvested with a forage or silage harvester (a forage or silage chopper). A silage or forage harvester refers to farm equipment used to make silage, which is grass, corn or other plant that has been chopped into small pieces, and compacted together in a storage silo, silage bunker, or in silage bags. A silage or forage harvester has a cutting mechanism, such as either a drum (cutterhead) or a flywheel with a number of knives fixed to it, which chops and transfers the chopped material into a receptacle that is either connected to the harvester or to another vehicle driving alongside. A forage harvester is preferred because it provides benefits over a sugar cane harvester or dry baled system. For example, a forage harvester provides higher density material than a sugar cane harvester, thereby allowing for more efficient transportation of the harvested material. In one embodiment, using a forage harvester results in harvested *sorghum* with a bulk density of about 400 kg/m$^3$, compared to sugarcane harvested with a sugarcane harvester with density of about 300 kg/m$^3$, and for *sorghum* harvested with a sugarcane harvester with a density of about 200 kg/m$^3$. In general, higher bulk density material is cheaper to transport, which tends to limit the geographical area in which cane-harvested crop can be sourced.

Thus, a forage harvester is an overall less expensive way to harvest the selected biomass, such as *sorghum*, than a cane harvester or dry baled system. Not to be bound by theory, it is believed the cost savings are due in part to higher material throughputs and the higher bulk density of the solid biomass harvested by a forage harvester. The solid biomass can be cut in any length. In one embodiment, the chop lengths of the harvester can be set to a range of about 3 mm to about 80 mm, preferably about 3 mm to about 20 mm, with examples of about 3 mm to about 13 mm chop lengths being most preferred. At these preferred chop lengths, there was not observable aqueous discharge in the forage harvester, so losses were minimal. When a chop length is selected, the harvester provides biomass with an average size or length distribution of about the chop length selected. In one embodiment, the average size distribution of the solid component exiting the recovery system can be adjusted as desired, which can be done by adjusting the chop length of the harvester.

At least one additive is added to the solid biomass to facilitate and/or expedite the conversion of appropriate carbohydrates into volatile organic compounds. After selected additive(s) have been added, the solid biomass can be referred to as prepared biomass material. In one embodiment, the prepared biomass material can comprise at least one or any combination of fermentable sugar-producing plants listed above. In a preferred embodiment, the selected additive(s) can be conveniently added using the harvester during harvest.

Embodiments of the invention provide for a scaled up operation to generate at least about 10 tons of the prepared biomass material in a particular harvest period. For embodiments using a forage harvester, the forage harvester assists in achieving the scaled up amount. In one embodiment, at least about 700 tons, preferably at least about 1 million tons, such as at least 1.2 million tons, or more preferably about at least 5 million tons of prepared biomass material is generated in a particular harvest window based on the growing conditions of a specific region, such as about 1 to 7 months in North America for *sorghum*. In one embodiment, up to 100 million tons of prepared biomass are generated in a particular harvest period.

The at least one additive can be added at any point during and/or after the harvest process. In a preferred embodiment using a forage harvester, additives are added to the solid biomass during the harvest process to generate a prepared biomass material. In particular, forage harvesters are designed for efficiently adding both solid and liquid additives during harvest. As mentioned above, the additives added include at least a microbe (e.g. a yeast), and optionally, an acid and/or an enzyme. In a preferred embodiment, the selected additive(s) are added as solutions. Additional details of the potential additives are further provided below.

For embodiments using a forage harvester or a similar equipment, the selected additive(s) can be added during harvest at all phases, such as before the intake feed rollers, during intake, at chopping, after chopping, through the blower, after the blower, in the accelerator, in the boom (or spout), and/or after the boom. In one embodiment where acid and enzyme are added, the acid is added near the intake feed rollers, and a microbe and the enzyme are added in the boom. In a particular embodiment, a Krone Big X forage harvester with a V12 motor with an about 30 ft wide header is used. In an embodiment using the Krone system, the acid is added as a solution through flexible tubing that discharged the solution just in front of the feed rollers. In this way, the liquid flow can be visually monitored, which showed the acid solution and solid biomass quickly mixed inside the chopping chamber. In another embodiment, the addition of acid was also demonstrated as a viable practice using a Case New Holland FX 58 forage harvester. In certain embodiments, the forage harvester used can include an onboard rack for containing additives, at least the one(s) selected to be added during harvest. In another embodiment, the selected additive(s) to be added during harvest may be towed behind the harvester on a trailer. For example, in one embodiment, it was demonstrated that a modified utility trailer equipped with tanks containing additive solutions of yeast, enzymes and acid can be employed with minimal interfering with normal operations of the harvester, thereby substantially maintaining the expected cost and duration of the harvest process. For example, a normal harvest configuration and biomass yield employing a silage harvester travelling at about 4 miles per hour maintains a similar rate of collection of about 4 miles per hour when equipped with certain additives as described above in one embodiment.

In embodiments of the present invention, the prepared biomass material is eventually transported to a storage facility where it is stored for a period of time to allow for production of at least one volatile organic compound from at least a portion of the fermentable sugar of the solid biomass. The details of the storage phase are further provided below. In certain embodiments, selected additive(s) can also be added at the storage facility. For example, in one embodiment, the selected additive(s) can be added during unloading or after the solid biomass has been unloaded at the storage facility. In one embodiment, a conveyance system is used to assist with the adding of selected additive(s) at the storage facility. Additive(s) added at the storage facility to solid biomass can be one(s) that have not been added or additional amount of one(s) previously added. Accordingly, selected additive(s) can therefore be added at any point from the start of the harvest process to prior to storage of the prepared biomass material at the storage area or facility, such as at points where the material is transferred.

As mentioned above, additive(s) for embodiments of the present invention include at least a microbe and optionally, an acid and/or an enzyme. Selected additive(s) can be added to the solid biomass in any order. In a preferred embodiment, an acid is added to the solid biomass before adding a microbe to prime the material to provide an attractive growth environment for the microbe.

In a preferred embodiment, acid is added to reduce the pH of the solid biomass to a range that facilitates and/or expedites selected indigenous or added microbial growth, which increases production of ethanol and/or volatile organic compounds. The acid can also stop or slow plant respiration, which consumes fermentable sugars intended for subsequent VOC production. In one embodiment, acid is added until the pH of the solid biomass is between about 2.5 and about 5.0, preferably in a range of about 3.7 to about 4.3, and more preferably about 4.2. The acid used can include known acids, such as sulfuric acid, formic acid, or phosphoric acid. The following Table 2 provides non-limiting examples of an acid that can be used individually or in combination.

TABLE 2

| Sulfuric Acid | Formic Acid | Propionic Acid | Malic Acid |
| Phosphoric Acid | Maleic Acid | Folic Acid | Citric Acid |

In a preferred embodiment, after the solid biomass has reached the desired pH with the addition of acid, a microbe is added. A microbe in the additive context refers at least to a living organism added to the solid biomass that is capable of impacting or affecting the prepared biomass material. One exemplary impact or effect from added microbe(s) includes providing fermentation or other metabolism to convert fermentable sugars from various sources, including cellulosic material, into ethanol or other volatile organic compounds. Another exemplary impact or effect may be production of certain enzyme(s) that help to deconstruct cellulose in the prepared biomass material into fermentable sugars which can be metabolized to ethanol or other VOC. Yet another exemplary impact or effect provided by a microbe includes production of compounds such as vitamins, co-factors, and proteins that can improve the quality, and thus value, of an eventual by-product that can serve as feed for animals. Further, microbial activity provides heat for the pile. Parts of the microbial cell walls or other catabolite or anabolite may also offer value-added chemicals that may be recovered by a recovery unit. These impacts and effects may also be provided by microbes indigenous to the solid biomass.

Any microbe that is capable of impacting or affecting the prepared biomass material can be added. In a preferred embodiment, the microbe(s) can include microbes used in the silage, animal feed, wine, and industrial ethanol fermentation applications. In one embodiment, the microbe selected includes yeast, fungi, and bacteria according to application and the desired profile of the organic molecule to be made. In a preferred embodiment, yeast is the selected microbe. In another embodiment, bacteria can be added to make lactic acid or acetic acid. Certain fungi can also be added to make these acids. For example, *Acetobacterium acetii* can be added to generate acetic acid; *Lactobacillus, Streptococcus thermophilus* can be added to generate lactic acid; *Actinobacillus succinogenes, Mannheimia succiniciproducens*, and/or *Anaerobiospirillum succiniciproducens* can be added to generate succinic acid; *Clostridium acetobutylicum* can be added to generate acetone and butanol; and/or *Aerobacter aerogenes* can be added to generate butanediol.

The following Table 3 provides non-limiting examples of preferred microbes, which can be used individually or in combination.

TABLE 3

| *Saccharomyces cerevisiae* | *Saccharomyces japonicas* | *Saccharomyces bayanus* | *Saccharomyces fermentatti* |
| *Saccharomyces exiguous* | *Saccharomyces chevalieri* | *Clostridium acetobutylicum* | *Clostridium amylosaccharobutyl propylicum* |
| *Clostridium propylbutylicum* | *Clostridium viscifaciens* | *Clostridium propionicum* | *Aerobacter* species |
| *Aerobacter aerogenes* | *Zymomonas mobilis* | *Zymomonas* species | *Clostridium* species |
| *Saccharomyces* species | *Bacillus* species | *Clostridium thermocellum* | *Lactobacillus buchneri* |
| *Lactobacillus plantarum* | *Enterococcus faecium* | *Pediococcus* species | *Propionibacteria* |
| *Acetobacterium acetii* | *Streptococcus thermophilus* | *Lactobacillus paracasei* | *Lactobacillus* species |
| *Actinobacillus succinogenes* | *Mannheimia succiniciproducens* | *Anaerobiospirillum succiniciproducens* | |

Preferred microbes also include *Saccharomyces cerevisiae* strains that can tolerate high ethanol concentrations and are strong competitors in its respective microbial community. The microbes may be mesophiles or thermophiles. Thermophiles are organisms that grow best at temperatures above about 45° C., and are found in all three domains of life: Bacteria, Archaea and Eukarya. Mesophiles generally are active between about 20 degrees C. and 45 degrees C. In an embodiment using a strain of *Saccharomyces cerevisiae*, the strain can come from a commercially available source such as Biosaf from Lesaffre, Ethanol Red from Phibro, and Lallamand activated liquid yeast. If the microbe is obtained from a commercial source, the microbe can be added according to the recommended rate of the provider, which is typically based on the expected sugar content per wet ton, where water is included in the mass calculation. The term "wet ton" refers at least to the mass unit including water. The recommended amount can be adjusted according to reaction conditions. The microbe added can comprise one strain or multiple strains of a particular microbe. In one embodiment, the microbes are added at a rate of up to 500 mL per wet ton of solid biomass.

In a particular embodiment using commercially available yeast, about 300 mL of Lallamand yeast preparation is added per wet ton of solid biomass. In another embodiment, an additional yeast strain can be added. For example, Ethanol Red can be added at a rate between about 0.001 kg/wet ton to about 0.5 kg/wet ton, particularly about 0.1 kg/wet ton. In yet another embodiment, another yeast strain can be added, e.g., Biosaf, at a rate between about 0.001 kg/wet tone to about 0.5 kg/wet ton, particularly about 0.1 kg/wet ton. It is understood that other amounts of any yeast strain can be added. For example, about 10%, about 20%, about 30%, about 40%, about 50%, about 60%, about 70%, about 80%, about 90%, about 1.5 times, about 2 times, about 2.5 times, or about 3 times of the provided amounts of microbes can be added.

In certain embodiments, an enzyme is further added. The enzyme can be one that assists in the generation of fermentable sugars from plant materials that are more difficult for the microbe to metabolize, such as different cellulosic materials, and/or to improve the value of an eventual by-product serving as animal feed, such as by making the feed more digestable. The enzyme can also be an antibiotic, such as a lysozyme as discussed further below. The enzyme added can include one type of enzyme or many types of enzymes. The enzyme can come from commercially available enzyme preparations. Non-limiting examples of enzymes that assist in converting certain difficult to metabolize plant materials into fermentable sugars include cellulases, hemicellulases, ferulic acid esterases, and/or proteases. Additional examples also include other enzymes that either provide or assist the provision for the production of fermentable sugars from the feedstock, or increase the value of the eventual feed by-product.

In certain embodiments, the enzymes that assist in converting certain difficult to metabolize plant materials into fermentable sugars can be produced by the plant itself, e.g. in-plantae. Examples of plants that can produce cellulases, hemicellulases, and other plant-polymer degrading enzymes may be produced within the growing plants are described in the patent publications and patent WO2011057159, WO2007100897, WO9811235, and U.S. Pat. No. 6,818,803, which show that enzymes for depolymerizing plant cell walls may be produced in plants. In another embodiment, ensilagement can be used to activate such plant produced enzymes as well as temper the biomass for further processing. One example is described in patent publication WO201096510. If used, such transgenic plants can be included in the harvest in any amount. For example, certain embodiments may employ in-plantae enzymes produced in plants by using particular transgenic plants exclusively as a feedstock, or incorporating the transgenic plants in an interspersed manner within like or different crops.

In certain embodiments that include such plant-polymer degrading enzymes, ethanol can be produced from cellulosic fractions of the plant. In a particular embodiment, when Novazymes CTEC2 enzyme was added to a *sorghum* storage system in excess of the recommended amount, about 100 times more than the recommended amount, about 152% of the theoretical ethanol conversion efficiency based on the initial free sugar content was achieved. While such an amount of enzymes can be added using commercially available formulations, doing so can be costly. On the other hand, such an amount of enzymes can be obtained in a more cost effective manner by growing transgenic plants that produce these enzymes at least interspersingly among the biomass crop.

The ethanol production from cellulose occurred during the storage phase, e.g., in silage and was stable for about 102 days of storage, after which the experiment was terminated. This demonstrates that, under the conditions of that particular experiment, an excess of such enzyme activity results in at least about 52% production of ethanol using fermentable sugars from cellulose. Not intended to be bound by theory, for certain embodiments, the immediate addition of acid during harvest in the experiment may have lowered the pH, thereby potentially inducing the enzyme activity, which otherwise could damage the plants if produced while the plants were still growing.

In a preferred embodiment, if an enzyme is added, the enzyme can be any family of cellulase preparations. In one embodiment, the cellulose preparation used is Novozymes Cellic CTec 2 or CTec 3. In another embodiment, a fibrolytic enzyme preparation is used, particularly, Liquicell 2500. If used, the amount of enzyme added to degrade plant polymer can be any amount that achieves the desired conversion of plant material to fermentable sugar, such as the recommended amount. In a particular embodiment, about 80,000 FPU to about 90,000,000 FPU, preferably about 400,000 FPU to about 45,000,000 FPU, more preferably about 800,000 FPU to about 10,000,000 FPU of enzyme is added per wet ton of biomass. The term "FPU" refers to Filter Paper Unit, which refers at least to the amount of enzyme required to liberate 2 mg of reducing sugar (e.g., glucose) from a 50 mg piece of Whatman No. 1 filter paper in 1 hour at 50° C. at approximately pH 4.8.

In certain other embodiments, selected additive(s) added can include other substances capable of slowing or controlling bacterial growth. Non-limiting examples of these other substances include antibiotics (including antibiotic enzymes), such as Lysovin (lysozyme) and Lactrol® (Virginiamycin, a bacterial inhibitor). Control of bacterial growth can allow the appropriate microbe to expedite and/or provide the production of volatile organic compounds. Antibiotic is a general term for something which suppresses or kills life. An example of an antibiotic is a bacterial inhibitor. In one embodiment, a selective antibiotic that is intended to impact bacteria and not other microbes is used. One example of a selective antibiotic is Lactrol, which affects bacteria but does not affect yeasts.

In a particular embodiment, if used, Lactrol can be added at rates of about 1 to 20 part-per-million (ppm) w/v (weight Lactrol per volume liquid) as dissolved in the water phase of the prepared biomass material, for example at about at about 5 ppm w/v. In an embodiment using an enzyme to control bacterial growth, lysozyme is preferably used. The lysozyme can come from a commercial source. An exemplary commercially available lysozyme preparation is Lysovin, which is a preparation of the enzyme lysozyme that has been declared permissible for use in food, such as wine.

The enzyme and/or other antibiotic material, if used, can be added independently or in conjunction with one another and/or with the microbe. In certain embodiments, other compounds serving as nutrients to the microbes facilitating and/or providing the volatile organic compound production can also be added as an additive. The following Table 4 provides non-limiting examples of other substances, including antibiotics, which can be added to the solid biomass.

TABLE 4

| Potassium Metabisulfite | Potassium Bicarbonate | FermaSure ® (from Dupont ™) - oxychlorine products including chlorite | Lysovin |

TABLE 4-continued

| Thiamin | Magnesium Sulfate | Calcium Pantothenate | Diammonium Phosphate |
|---------|-------------------|----------------------|----------------------|
| Ammonia | Antibiotics | Lactrol | Biotin |

Yeasts and other microbes that are attached to solids individually, as small aggregates, or biofilms have been shown to have increased tolerance to inhibitory compounds. Not intended to be bound by theory, part of the long-term fermentation may be possible or enhanced by such microbial-to-solids binding. As such, the prepared biomass material that includes the microbe optimized for microbial binding as well as additives that may bind microorganisms can experience a greater extent of fermentation and or efficiency of fermentation. Substances providing and/or facilitating long term fermentation is different from substances that increase the rate of fermentation. In certain embodiments, an increase in the rate of fermentation is not as an important factor as the long-term fermentation, particularly over a period of many weeks or months.

The following provides particular amounts of additives applied to one specific embodiment. If used, the rate and amount of adding an acid varies with the buffering capacity of the particular solid biomass to which the particular acid is added. In a particular embodiment using sulfuric acid, 9.3% w/w sulfuric acid is added at rates of up to about 10 liter/ton wet biomass, for example at about 3.8 liter/ton wet biomass to achieve a pH of about 4.2. In other embodiments, the rate will vary depending on the concentration and type of acid, liquid and other content and buffering capacity of the particular solid biomass, and/or desired pH. In this particular embodiment, Lactrol is added at a rate of about 3.2 g/wet ton of solid biomass. Yeasts or other microbes are added according to the recommended rate from the provider, such as according to the expected sugar content per wet ton. In one particular embodiment, Lallemand stabilized liquid yeast is added at about 18 fl oz per wet ton, and Novozymes Cellic CTec2 is added at about 20 fl oz per wet ton.

In a preferred embodiment, selected additive(s) are added to the solid biomass stream during harvest according to aspects of the invention described above to generate the prepared biomass material. Preferably, the prepared biomass material is transported to a storage facility to allow for conversion of carbohydrates of the prepared biomass material into volatile organic compounds of the desired amount and/or await recovery of the volatile organic compounds. Any suitable transportation method and/or device can be used, such as vehicles, trains, etc, and any suitable method to place the prepared biomass material onto the transportation means. Non-limiting examples of vehicles that can be used to transport the biomass material include end-unloading dump trucks, side-unloading dump trucks, and self-unloading silage trucks. In a preferred embodiment, a silage truck is used. In embodiments using a forage harvester to collect the biomass, transportation of such solid biomass is more efficient than transportation of materials collected by conventional means, such as sugar cane billets, because the bulk density is higher in the solid biomass cut with a forage harvester. That is, materials chopped into smaller pieces pack more densely than materials in billets. In one embodiment, the range of bulk densities in a silage truck varies between about 150 kg/m$^3$ and about 350 kg/m$^3$, for example about 256 kg/m$^3$. Because in certain embodiments, all selected additives are added during harvest, preferably on the harvester, the microbe may begin to interact with the biomass during transportation, and in this way transportation is not detrimental to the overall process.

The biomass, whether prepared or not, is delivered to at least one storage area or facility. The storage facility can be located any distance from the harvest site. Selected additive(s) can be added if they have not been added already or if additional amounts or types need to be further added to generate the prepared biomass material. In a preferred embodiment, the prepared biomass is stored in at least one pile on a prepared surface for a period of time. The facility can incorporate man-made or natural topography. Man-made structures can include existing structures at the site not initially designated for silage, such as canals and water treatment ponds. Non-limiting examples of a prepared surface includes a concrete, asphalt, fly ash, or soil surface. The at least one pile can have any dimension or shape, which can depend on operating conditions, such as space available, amount of biomass, desired storage duration, etc.

In a particular embodiment, at least one pile of prepared biomass material is formed having a height in a range of about 10 feet to about 30 feet. In another embodiment, the height of the at least one pile is greater than 30 feet. In one embodiment, at least one pile of prepared biomass material contains at least about 10 tons of prepared biomass material, which can be wet tons. In another embodiment, at least one pile contains 25,000 tons (or wet tons) of prepared biomass material. In another embodiment, the at least one pile of prepared biomass material contains at least about 100,000 tons (or wet tons) of prepared biomass material. In yet another embodiment, the least one pile of prepared biomass material contains at least about 1,000,000 tons or (wet tons), such as 1,200,000 wet tons, of prepared biomass material. In one embodiment, the at least one pile contains up to about 10,000,000 tons, and in another embodiment, up to 100,000,000 tons (or wet tons) of prepared biomass material.

The conversion process of fermentable sugars is an exothermic reaction. Too much heat, however, can be detrimental to the conversion process if the temperature is in the lethal range for the microbes in the prepared biomass material. However, in an embodiment using about 700 wet tons of biomass and piling up to about 12 feet, ethanol production and stability were satisfactory. Therefore larger piles will likely not suffer from overheating. In one embodiment, an inner portion of the pile maintains a temperature in a range of about 20 degrees C. to about 60 degrees C. for microbes of all types, including thermophiles. In an embodiment not employing thermophiles, an inner portion of the pile maintains a temperature in a range of about 35 degrees C. to about 45 degrees C.

The prepared biomass material that is stored as at least one pile at the storage facility can also be referred to as a wet stored biomass aggregate. After addition of the selected additive(s), at least a portion of the solid biomass is converted to volatile organic compounds, such as fermentation of sugars into ethanol. In one embodiment, the prepared biomass material is stored for a period of time sufficient to achieve an anaerobiasis environment. In a preferred embodiment, the anaerobiasis environment is achieved in about 24 hours. In another embodiment, the anaerobiasis environment is achieved in more than about 4 hours. In yet another embodiment, the anaerobiasis environment is achieved in up to about 72 hours.

The pile can be free standing or formed in another structure, such as a silage bunker, designed to accept silage, including provisions to collect aqueous runoff and leachate, placement of a tarp over the biomass, and to facilitate both efficient initial silage truck unloading into the bunker as well as removal of the biomass year around. The individual bunkers may be sized at about the size to support annual feedstock requirements of about 700 wet tons to 100,000,000 wet tons or more. For example, the storage facility may have 50 bunkers, where each individual bunker can accept 100,000 wet tons of prepared biomass material for a total of a maximum of about 5,000,000 wet tons of stored material at any one time. Other exemplary inventory amounts of prepared biomass material at any one storage facility include at least about 10 tons, about 25,000 tons, about 100,000 tons, about 1,000,000 tons, about 1,200,000 tons, about 1,500,000 tons, about 10,000,000 tons, and up to about 100,000,000 tons. In a preferred embodiment where ethanol is the volatile organic compound of choice, about 14 gallons to about 16 gallons of ethanol is recovered per one wet ton of prepared biomass material. The provided numbers are exemplary and not intended to limit the amount of prepared biomass material a storage facility can accommodate.

In a particular embodiment, the storage pile further includes a leachate collection system. In one embodiment, the collection system is used to remove leachate collected from the storage pile. For example, the leachate collection system can be adapted to remove liquid from the pile at certain points during the storage period. In another embodiment, the leachate collection system is adapted to circulate the liquid in the storage pile. For example, circulation can involve taking at least a portion of the recovered liquid and routing it back to the pile, preferably at or near the top portion. Such recirculation allows for longer retention time of certain portions of the liquids in the pile, even as the recovery phase of the prepared biomass material begins and portions of the non-liquid component of the prepared biomass material are sent to the recovery unit. The longer retention time results in longer microbial reaction time, and hence, higher concentrations of organic volatile compounds, such as ethanol.

Any suitable leachate collection system known to those skilled in the art can be employed as described. In a particular embodiment, the leachate collection system comprises at least one trough along the bottom of the pile, preferably positioned near the middle, of the storage pile or bunker if one is used, where the storage pile is prepared at a grade designed to direct liquid from the prepared biomass material to the trough and out to a desired collection receptacle or routed to other applications.

In another embodiment, the leachate collection system comprises one or more perforated conduits, preferably pipes made of polyvinyl chloride (PVC), that run along the bottom of the pile to allow the liquid collected in the conduits to be directed away from the pile.

In one embodiment, as the prepared biomass material is added to the bunker or laid on top of the prepared surface, a tractor or other heavy implement is driven over the pile repeatedly to facilitate packing. In one embodiment, the packing ranges from about 7 lbs/ft$^3$ to about 50 lbs/ft$^3$ per cubic foot for the prepared biomass material. In a preferred embodiment, the packing is from about 30 lbs/ft$^3$ to about 50 lbs/ft$^3$, particularly about 44 lbs/ft$^3$. In one embodiment, the compacting of the prepared biomass material in a pile facilitates and/or allows an anaerobiasis environment to be achieved in the preferred time periods described above. In another embodiment, after the packing is performed or during the time the packing is being performed, an air impermeable membrane is placed on the pile, typically a fit for purpose plastic tarp. In a particular embodiment, the tarp is placed on the pile as soon as is practical. For instance, the tar is placed on the pile within a 24-hour period.

In one embodiment, the prepared biomass material is stored for at least about 24 hours and preferably at least about 72 hours (or 3 days) to allow for production of volatile organic compounds, such as ethanol. In one embodiment, the prepared biomass material is stored for about three days, preferably ten days, more preferably greater than ten days. In one embodiment, the time period for storage of the prepared biomass is about 1 day to about 700 days, preferably about 10 to 700 days. In another embodiment, the biomass material is stored for up to about three years. In one embodiment, the prepared biomass material is stored for a time period sufficient to allow a conversion efficiency of sugar to at least one volatile organic compound of at least about 95% of the theoretical production efficiency as calculated through a stoichiometric assessment of the relevant biochemical pathway. In another embodiment, the prepared biomass material is stored for a time period sufficient to allow a calculated conversion efficiency of sugar to at least one volatile organic compound of at least about 100%. In yet another embodiment, the prepared biomass material is prepared with certain additives, such as enzymes, that allow a calculated conversion efficiency of sugar to at least one volatile organic compound of up to about 150% of the theoretical value based on the initial amount of available fermentable sugars. Not intended to be bound by theory, it is believed that, at or above 100% efficiency, the volatile organic compound(s) are produced from both the initially available fermentable sugars and fermentable sugars from cellulosic or other polymeric material in the prepared biomass material, which can be achieved by enzymatic hydrolysis or acid hydrolysis facilitated by certain additive(s) applied to the biomass.

The produced volatile organic products, such as ethanol, remain stable in the stored prepared biomass material for the duration of the storage period. In particular, the prepared biomass material can be stored up to 700 days without significant degradation to the volatile organic compounds. "Significant" in this context refers at least to within the margin of error when measuring the amount or concentration of the volatile organic compounds in the prepared biomass material. In one embodiment, the margin of error is 0.5%. It has been demonstrated that ethanol remains stable in the pile after at least about 330 days with no significant ethanol losses observed. This aspect of embodiments of the present invention is important because it provides for at least eight months of stable storage, which enables year-round VOCs production and recovery with a harvest window of only about four months. Embodiments of the invention provide significant advantages over the conventional just-in-time processing that would only be able to operate during the four months harvest window per year. That is, embodiments of the invention allow a plant to operate year-round using only a four-month harvest window, thereby reducing capitals cost for a plant of the same size as one used for just-in-time processing.

Also, in an embodiment employing a tarp, it is envisioned that placing soil or other medium around and on the tarp edges to 1) provide weight for holding the tarp down; and also 2) to act as a biofilter of the off-gas from the pile. In such an embodiment, biofilters are efficient for organics and carbon monoxide detoxification/degradation. The prepared biomass material can also be stored as compressed modules, drive over piles, bunkers, silos, bags, tubes, or wrapped bales or other anaerobic storage system.

In one embodiment, the off-gas stream from a pile of prepared biomass material was monitored, and it was found that only small levels of organics, and also very low levels of nitrogen oxides, were present. For example, Tables 5.1, 5.2, and 5.3 below show the analysis of various off-gas samples collected during the storage phase of one implementation of certain embodiments of the invention. The designation "BDL" refers to an amount below detectable limit. Summa and TEDLAR® refer to gas sampling containers commercially available.

TABLE 5.1

| Container type | Container ID | % H$_2$ | % O$_2$ | % N$_2$ | % CH$_4$ | % CO$_2$ | % H$_2$O | Normalized CO2 |
|---|---|---|---|---|---|---|---|---|
| TEDLAR ® bag | A | BDL | 1.72 | 7.84 | BDL | 95.90 | 5.23 | 85.21 |
| TEDLAR ® bag | B | BDL | 2.30 | 9.12 | BDL | 89.97 | 5.97 | 82.62 |
| TEDLAR ® bag | C | BDL | 0.71 | 3.57 | BDL | 97.45 | 5.54 | 90.18 |
| TEDLAR ® bag | D | BDL | 0.72 | 3.18 | BDL | 97.50 | 5.97 | 90.14 |
| TEDLAR ® bag | E | BDL | 1.86 | 7.24 | BDL | 91.75 | 7.64 | 83.26 |
| Summa Container | EQ #8 | 0.01 | 5.74 | 22.14 | 0.07 | 73.74 | 5.28 | 66.84 |
| Summa Container | EQ #13 | 0.09 | 3.28 | 12.89 | 0.33 | 84.48 | 5.66 | 78.18 |
| Summa Container | EQ #16 | 0.12 | 3.30 | 13.01 | 0.12 | 84.65 | 4.99 | 78.70 |

TABLE 5.2

| Container type | Container ID | % O$_2$ | ppmv CO | % CO$_2$ | ppmv HC | ppmv NO | ppmv NO$_2$ | ppmv NO$_X$ | ppmv SO$_2$ |
|---|---|---|---|---|---|---|---|---|---|
| TEDLAR ® bag | A | 1.6 | 13 | 72.7 | 104 | 3.8 | 1.90 | 5.70 | BDL |
| TEDLAR ® bag | B | 4.4 | 19 | 66.2 | 739 | 2.5 | 122.90 | 125.40 | 6 |
| TEDLAR ® bag | C | 0.6 | 29 | 75.3 | 158 | 8.9 | 27.20 | 36.10 | 4 |
| TEDLAR ® bag | D | 0.6 | 35 | 75.7 | 222 | 7.9 | 56.50 | 64.40 | 5 |
| TEDLAR ® bag | E | 4.1 | 35 | 66.8 | 423 | 3.0 | 20.30 | 23.90 | 4 |

TABLE 5.3

| Container type | Container ID | ppmv CH2O | ppmv C2H4O | ppmv methanol | ppmv 2-propanol | ppmv ethanol | ppmv propanol |
|---|---|---|---|---|---|---|---|
| TEDLAR ® bag | A | 386 | 870 | 63.4 | 0.593 | 78.5 | BDL |
| TEDLAR ® bag | B | BDL | 1299 | 678 | 0.186 | 1065 | 15.2 |
| TEDLAR ® bag | C | 18.2 | 590 | 89.2 | 2.784 | 171 | 6.098 |
| TEDLAR ® bag | D | BDL | 941 | 170 | 3.031 | 264 | 7.648 |
| TEDLAR ® bag | E | BDL | 819 | 389 | 2.512 | 634 | 11.3 |

Embodiments of the present invention, although relatively uncontained in the bunker, should be environmentally benign. Even so, certain aspects of the present invention fit well with using soil or other media as a biofilter placed around and on the bunkers because the escape of gas from under the tarp is radial in nature. As such, the vapors have a higher amount of surface area in contact with the edges of the pile. In embodiments using a biofilter, vapor phase releases pass through the biofilter (such as soil or compost) placed near the edge mass before entering into the atmosphere. The biofilter retains many potential environmental pollutants and odors released by the storage pile, and it eliminates or greatly reduces the potentially harmful off-gases released from the storage pile.

In one embodiment, the prepared biomass material is stored until it contains no more than about 80 wt % liquid. The prepared biomass material is stored until it contains at least about 4 to about 5% higher than initial content. At this stage, the wet stored biomass aggregate is not considered "beer" yet since it still contains over about 20% solids. In one embodiment, the prepared biomass material is stored until it contains between about 2 wt % and about 50 wt % ethanol, and preferably between about 4 wt % and about 10 wt % ethanol. The balance of the liquid is primarily water but can contain many other organic compounds, such as acetic acid, lactic acid, etc.

Embodiments of the present invention allow the solid biomass to be harvested in a much shorter harvest window than typical sugar cane juicing operations, which allows for 1) a much larger geographic area where the facilities could be placed, 2) harvest of the crop when the crop has its highest yield potential, 3) harvest of the crop at its highest sugar concentration potential, 4) shorter harvest window still economical, and 5) decoupling the need for taking the juice from the biomass for fermentation.

Moreover, aspects of the present invention allow for larger scale operations, such as in the industrial or commercialization range. In one embodiment, at least about 10 tons of prepared biomass material is generated by adding a microbe, an acid, and optionally an enzyme to the solid biomass. Other amounts are provided above.

The preparation of the biomass material of embodiments of the invention can also be generally referred to as solid state fermentation. Once the prepared biomass material has been stored for the desired amount of time and/or contains a desired concentration of volatile organic compounds, such as ethanol, it can be routed to the recovery system for recovery of particular volatile organic compounds. The recovery system and storage facility can be located any distance from one another. Embodiments of systems and methods described herein allow flexibility in the geographical location of both and their locations relative to each other. In a particular embodiment, the recovery system is located about 0.5 to about 2 miles from the storage facility. Any suitable method and/or equipment can be used to transfer the prepared biomass material from the storage facility to the recovery system. In one embodiment, a feed hopper is used. In one embodiment, a silage facer, a front end loader or payloader, a sweep auger or other auger system can be used to place the prepared biomass material into the feed hopper. The material can be placed directly into the feed hopper or it can be transferred to by conveyer system, such as belt system. The feed hopper containing the prepared biomass material can then be driven to the recovery system.

The recovery system is solventless and uses a superheated vapor stream to vaporize the liquid in the prepared biomass material into a gas component, which can then be collected. A super-heated vapor is a vapor that is heated above its saturation temperature at the pressure of operation. In a preferred embodiment, after the recovery system reaches steady state, the superheated vapor stream comprises only vapor previously evaporated from the prepared biomass material, so that no other gas is introduced, thereby reducing the risk of combustion of the volatile organic compounds and/or dilution of the recovered product stream of volatile organic compounds. The remaining solid component is discharged from the system and can have various subsequent uses. A portion of the vapor is removed as product and the remainder is recycled back for use in transferring heat to fresh incoming prepared biomass material. The super-heated vapor directly contacts the biomass transferring energy and vaporizing the liquid present there. The heat or thermal energy source does not directly contact the prepared biomass material. Thus, the VOC recovery system can also be described as providing "indirect" heat contact.

To provide solventless recovery of volatile organic compounds, the recovery system comprises a compartment that allows superheated vapor to flow in a continuous manner, i.e., as a stream. In one embodiment, the compartment has a loop shape. In another embodiment, the compartment comprises a rotating drum. The compartment has an inlet through which the prepared biomass material can enter. In one embodiment, the inlet comprises a pressure tight rotary valve, plug screw, or other similar device, which can assist in separating the prepared biomass material to increase the surface area exposed to the superheated vapor stream.

In yet another embodiment, the system comprises a dewatering mechanism to remove at least a portion of the liquid in the prepared biomass material before the liquid is vaporized. The liquid removal can occur before and/or while the prepared biomass material enters the compartment. The liquid from the prepared biomass material contains at least one volatile organic compound, which can be recovered by further processing the liquid, such as feeding the liquid to a distillation column. The liquid can be routed directly to further processing unit, such as a distillation column. Alternatively or in addition to, the system further includes a collection unit to collect the liquid removed from the prepared biomass material. Any portion of the collected liquid can then be further processed.

In one embodiment, the dewatering mechanism comprises a component adapted to squeeze the liquid from the prepared biomass material. In such an embodiment, the squeezing can be performed while the prepared biomass material is being fed into the compartment. For instance, the inlet can comprise a squeezing mechanism to squeeze liquid from the prepared biomass material as it is introduced into the compartment. Alternatively or in addition to, the squeezing can be performed separately before the prepared biomass material enters the compartment. A non-limiting example of such a squeezing mechanism is a screw plug feeder.

In one embodiment, the liquid removal mechanism comprises a mechanical press. Non-limiting examples of types of mechanical presses include belt filter presses, V-type presses, ring presses, screw presses and drum presses. In a particular embodiment of a belt filter press, the prepared biomass material is sandwiched between two porous belts, which are passed over and under rollers to squeeze moisture out. In another particular embodiment, a drum press comprises a perforated drum with a revolving press roll inside it that presses material against the perforated drum. In yet another embodiment, in a bowl centrifuge, the material enters a conical, spinning bowl in which solids accumulate on the perimeter.

The compartment provides a space where the superheated vapor stream can contact the prepared biomass material to vaporize the liquid from the prepared biomass material. The vaporization of at least a portion of the liquid provides a gas component and a solid component of the prepared biomass material. The system further comprises a separating unit where the solid component of the prepared biomass material can be separated from the gas component, so each component can be removed as desired for further processing. In one embodiment, the separating unit comprises a centrifugal collector. An example of such centrifugal collector is high efficiency cyclone equipment. In a preferred embodiment, the separating unit also serves as an outlet for the solid component. For example, the separating unit can discharge the solid component from the solventless recovery system. There is a separate outlet for the gas component where it can exit the system for further processing, such as distillation. In one embodiment, the separating unit is further coupled to a second pressure tight rotary valve or the like to extrude or discharge the solid component. In one embodiment, the superheated vapor is maintained at a target or desired temperature above its saturation temperature by a heat exchange component coupled to a heat source where the superheated vapor does not contact the heat source. The heat transfer between the heat source and the system occurs via convection to the superheated vapor. In one embodiment, the heat source can include electrical elements or hot vapors through an appropriate heat exchanger. In one embodiment, the operating pressure is in a range from about 1 psig to about 120 psig. In a preferred embodiment, the operating pressure is in a range from about 3 psig to about 40 psig. In a particularly preferred embodiment, the system is pressurized at an operating pressure of about 60 psig to force the vapor component from the system.

In one embodiment, at start up of the recovery system, the prepared biomass material is introduced into the compartment via the inlet. Steam is initially used as the superheated vapor to initially vaporize the liquid in the prepared biomass material. The superheated vapor continuously moves through the compartment. When the prepared biomass material enters the superheated vapor stream, it becomes fluidized where it flows through the compartment like a fluid. As the prepared biomass material is introduced, it comes into contact with the superheated vapor stream. Heat from the superheated vapor is transferred to the prepared biomass material and vaporizes at least a portion of the liquid in the prepared biomass material and is separated from the solid component, which may still contain moisture. The gas component contains volatile organic compound(s) produced in the prepared biomass material. In a preferred embodiment, as liquid from the prepared biomass material begins to vaporize, at least a portion of the vaporized liquid can be recycled in the system as superheated fluid. That is, during any one cycle, at least a portion of the vaporized liquid remains in the compartment to serve as superheated vapor instead of being collected for further processing, until the next cycle where more prepared biomass material is fed into the system.

In a preferred embodiment, during the initial start up procedure, the superheated fluid can be purged as needed, preferably continuously (intermittently or constantly), until steady state is achieved where the superheated vapor comprises only vaporized liquid of the prepared biomass material. The gas component and solid component can be collected via the respective outlet. Heat can be added continuously (intermittently or constantly) to the system via the heat exchanger coupled to the heat source to maintain the temperature of the superheated vapor, to maintain a desired operating pressure in the system, or to maintain a target vaporization rate. Various conditions of the system, such as flow rate of the superheated vapor stream, pressure, and temperature, can be adjusted to achieve the desired liquid and/or volatile organic compounds removal rate.

In one embodiment, the collected gas component is condensed for further processing, such as being transferred to a purification process to obtain a higher concentration of the volatile organic compound(s) of choice. In a preferred embodiment, the collected gas component is fed directly into a distillation column, which provides savings of energy not used to condense the gas component. In another embodiment, the gas component is condensed and fed to the next purification step as liquid.

In one embodiment, before entering the recovery phase, the prepared biomass material has an initial liquid content of about at least 10 wt % and up to about 80 wt % based on the biomass material. In a particular embodiment, the initial liquid content is at least about 50 wt % based on the biomass material. In one embodiment, the initial liquid content comprises from about 2 to 50 wt %, and preferably from about 4 to 10 wt % ethanol based on the initial liquid content.

In one embodiment, the solid component collected contains from about 5 wt % to about 70 wt %, and preferably from about 30 wt % to about 50 wt %, liquid depending on the ethanol removal target. In another component, the collected gas component contains between about 1 wt % and about 50 wt % ethanol, preferably between about 4 wt % and about 15 wt % ethanol. In one embodiment, the recovery system recovers from about 50% to about 100% of the volatile organic compounds contained in the prepared biomass material. The residence time of the prepared biomass varies based on a number of factors, including the volatile organic compound removal target. In one embodiment, the residence time of the prepared biomass material in the compartment is in a range of about 1 to about 10 seconds. In one embodiment, the recovery system can be operated between about 0.06 barg and about 16 barg. The term "barg" refers to bar gauge as understood by one of ordinary skill in the art, and 1 bar equals to 0.1 Mega-Pascal. In one embodiment, the gas in the recovery system has a temperature in a range of about 100° C. to about 375° C., particularly from about 104° C. to about 372° C., and the solid component exiting the system has a temperature of less than about 50° C. The collected solid component can be used in other applications. Non-limiting examples include animal feed, feed for a biomass burner to supply process energy or generate electricity, or further converted to ethanol by means of a cellulosic ethanol process (either re-ferment in a silage pile, or feed to a pre-treatment unit for any cellulosic ethanol process) or a feed for any other bio-fuel process requiring ligno-cellulosic biomass.

The operating conditions of the solventless recovery system include at least temperature, pressure, flow velocity, and residence time. Any one or combination of these conditions can be controlled to achieve a target or desired removal target, such as the amount of the initial liquid content removed or the amount of the liquid remaining in the separated liquid component exiting the recovery system. In one embodiment, at least one operating condition is controlled to achieve removal of about 10-90 wt %, preferably about 45-65 wt %, and more preferably about 50 wt %, of the initial liquid content.

In a preferred embodiment, increasing the temperature of the system at constant pressure will cause the liquid in the biomass to be vaporized more quickly and thus for a given residence time will cause a higher percentage of the liquid in the biomass to be evaporated. The vapor flow rate exiting the system has to be controlled to match the rate of vaporization of liquid from the biomass in order to achieve steady state and can also be used as a mechanism to control the system pressure. Increasing the system pressure will cause more energy to be stored in the vapor phase in the system which can then be used to aid in further processing or to help move the vapor to the next downstream processing unit. Increasing the biomass residence time in the system causes more heat to be transferred from the vapor phase to the biomass resulting in more liquid being vaporized.

In a specific exemplary embodiment, the recovery system comprises a closed loop pneumatic superheated steam dryer, which can be obtained from commercially available sources. In one embodiment, the closed loop pneumatic superheated steam dryer is an SSD™ model of GEA Barr-Rosin Inc. Other suitable commercially available equipment include the Superheated Steam Processor, SSP™ from GEA Barr-Rosin Inc, the Ring Dryer from several companies including GEA Ban-Rosin Inc. and Dupps; the Airless Dryer from Dupps; the QuadPass™ Rotary Drum Dryer from DuppsEvactherm™, Vacuum Superheated Steam Drying from Eirich; the rotary drum dryer using superheated vapor from Swiss Combi Eco-dry; and the airless dryer from Ceramic Drying Systems Ltd.

Still other types of indirect dryers that could serve as the volatile organics recovery unit for this process are batch tray dryers, indirect-contact rotary dryers, rotating batch vacuum dryers, and agitated dryers. The basic principle for these dryers is that they will be enclosed and attached to a vacuum system to remove vapors from the solids as they are generated (also by lowering the pressure with the vacuum the volatiles are removed more easily). The wet solids contact a hot surface such as trays or paddles, the heat is transferred to the wet solids causing the liquids to evaporate so they can be collected in the vacuum system and condensed.

FIG. 1 illustrates an exemplary VOC recovery system and process employing a superheated steam dryer, referenced as system 100. In a particular embodiment, the superheated steam dry can be obtained from GEA Barr-Rosin Inc. In FIG. 1, prepared biomass material 1 containing ethanol and/or other VOCs following solid state fermentation in the silage piles is fed into compartment 3 through input 2. In the particular embodiment shown, input 2 comprises a screw extruder. As shown in FIG. 1, at least a portion of the liquid of the prepared biomass material 1 is removed prior to entering compartment 3. The dewatering mechanism can be a screw plug feeder through which the prepared biomass material 1 passes. At least a portion of the liquid removed from biomass material 1 can be routed directly to distillation step 11 via stream 15 without going through recovery system 100. Optionally, a delumper can be coupled to the output of the dewatering mechanism can be used to facilitate introduction of the dewatered biomass material into compartment 3.

Referring to FIG. 1, recovery system 100 comprises compartment 3, which can be pressurized, shown as a conduit that has an appropriate diameter, length and shape, adapted to provide the desired operating conditions, such as residence time of prepared biomass material 1, heat transfer to the superheated vapor, and operating pressure and temperature. After entering compartment 3, during steady state operation, prepared biomass material 1 contacts superheated vapor flowing through system 100 at a desired temperature and becomes fluidized. As described above, in a preferred embodiment, the superheated vapor, or at least a portion thereof, is vapor component obtained from prepared biomass materials previously fed into system 100 for VOC recovery.

The fluidized biomass flows through compartment 3 at a target flow rate and remains in contact with the superheated vapor for a target residence time sufficient to evaporate the desired amount of liquid from prepared biomass material 1. In the embodiment shown, the flow of the superheated vapor and prepared biomass material 1 through system 100 is facilitated by system fan 14. System 100 can have one or more fans. The flow rate or velocity of the superheated vapor and biomass material 1 can be controlled by system fan 14. Biomass material 1 flows through compartment 3 and reaches separating unit 4, which is preferably a cyclone separator, where a vapor component and a solid component of biomass material 1 are separated from each other. As shown, the vapor component is routed away from the solid component via overhead stream 5 and the remaining portion of biomass material 1 is considered a solid component, which is discharged from separating unit 4 as solid component 7, preferably by screw extruder 6. At least a portion of the discharged solid component 7 can be used as animal feed, burner fuel, or biomass feedstock for other bio-fuels processes.

Referring to FIG. 1, a portion of the vapor component, referenced as stream 8, is retained and recycled as a portion of the superheated vapor used to vaporize newly introduced prepared biomass material. In the embodiment shown, the retained vapor component in stream 8 is routed through heat exchanger 9 to heat it to the target operating temperature. The heat source can include steam, electricity, hot flue gases or any other applicable heating source known to those skilled in the art.

In a preferred embodiment, the temperature is controlled such that the pressure in the system is maintained at the target and there is adequate energy present to evaporate the desired amount of liquid. The pressure can also be controlled by the flow rate of the superheated vapor stream and the heat input to heat exchanger 9. Preferably, recovery system 100 operates continuously where prepared biomass material 1 is continuously fed at a desired rate, and vapor component 10 and solid component 6 are continuously removed at a continuous rate. In a preferred embodiment, "fresh" vapor component 8 from one run is retained continuously at a target rate to be used as the superheated vapor stream for the next run. Any of these rates are adjustable to achieve the desired operating conditions. As mentioned, system fan 14 circulates the superheated vapor stream through system 100 and can be adjusted to obtain the target flow rate or velocity.

Referring to FIG. 1, the remaining portion of vapor component stream 5, represented as numeral 10 is routed to a distillation step 11. Depending on the distillation configuration, vapor component portion 10 may be condensed before further purification or preferably fed directly into the distillation column as a vapor. In a preferred embodiment, the distillation product from distillation step 11 has an ethanol content of about 95.6 wt % ethanol (the ethanol/water azeotrope), which can further be purified to above about 99 wt % using common ethanol dehydration technology, which is shown as step 12. The final ethanol product 13 will then typically be used as a biofuel for blending with gasoline.

Figure 2:
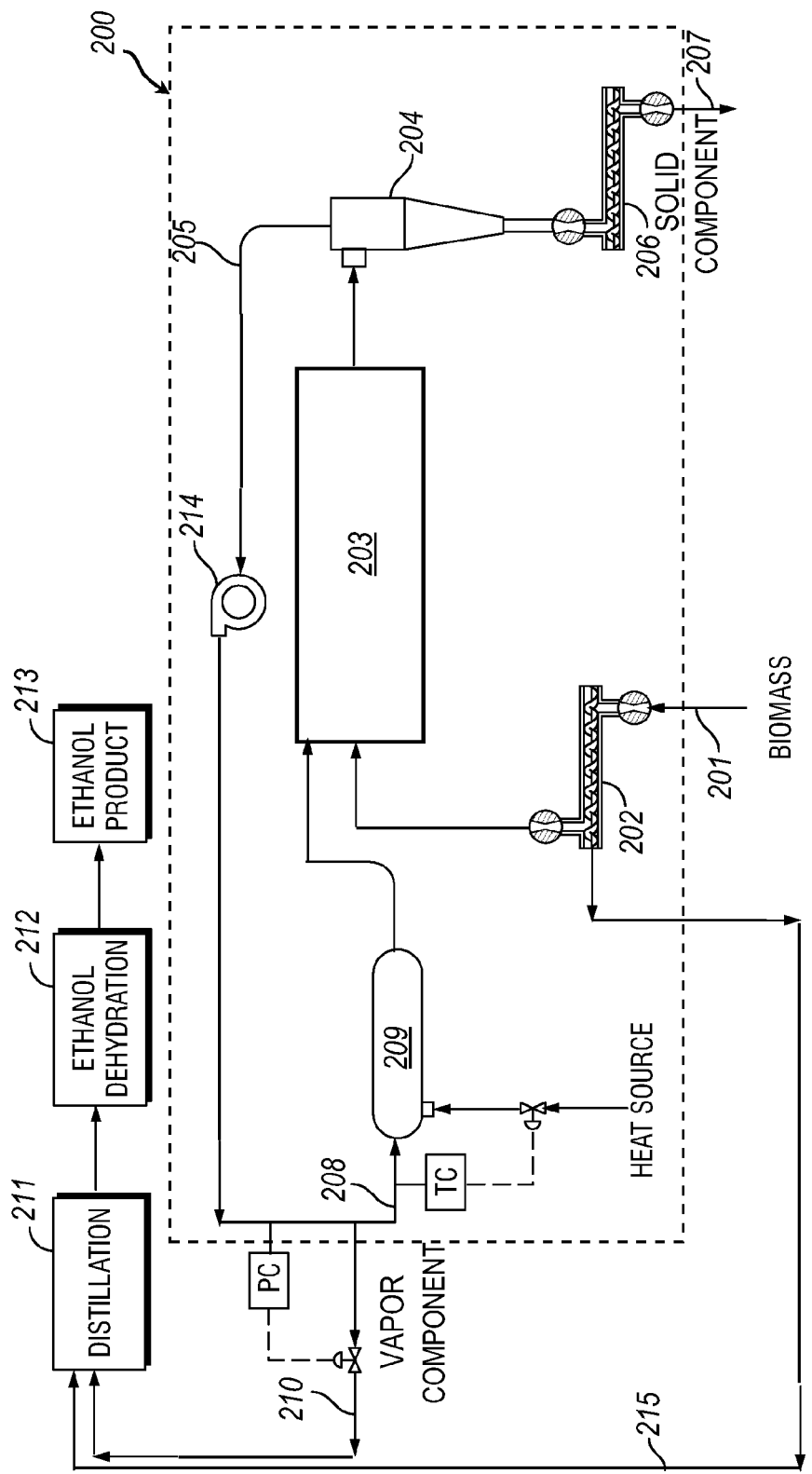
FIG. 2 is a diagram of another embodiment to process biomass material according to certain aspects of the present invention.

FIG. 2 illustrates another exemplary recovery system and process employing a superheated steam dryer, referenced as system 200 that is representative of the Ring Dryer provided by various manufacturers. Prepared biomass material 201 is fed into system 200 through input 202, which preferably comprises a screw extruder. In one embodiment, least a portion of the liquid of the prepared biomass material 201 is removed prior to entering system 200. The dewatering mechanism can be a screw plug feeder through which the prepared biomass material 201 passes. At least a portion of the liquid removed from biomass material 201 can be routed directly to distillation step 211 via stream 215 without going through recovery system 200. Optionally, a delumper can be coupled to the output of the dewatering mechanism can be used to facilitate introduction of the dewatered biomass material into compartment 203.

Referring to FIG. 2, recovery system 200 comprises compartment 203, which preferably comprises a rotating drum that provides the target operating conditions for VOC recovery, including residence time of prepared biomass material 201, heat transfer to the superheated vapor, and operating pressure and temperature. After entering compartment 203, during steady state operation, prepared biomass material 201 contacts superheated vapor flowing through system 200 at the operating temperature and flow rate and becomes fluidized. As described above, in a preferred embodiment, the superheated vapor, or at least a portion thereof, is the vapor component obtained from prepared biomass material previously fed into system 200 for VOC recovery. The fluidized biomass flows through compartment 203 at a target flow rate and remains in contact with the superheated vapor for the target residence time to achieve the target vaporization of liquid from the biomass. The fluidized biomass then reaches separating unit 204, which is preferably a cyclone separator, where the vapor component and solid component are separated from each other. As shown, the vapor component is routed away from the solid component through overhead stream 205, and solid component 207 is discharged from separating unit 204. As shown, solid component 207 exits system 100 via extruder 206 and can have subsequent uses as mentioned above. A portion of the vapor component, referenced as stream 208, is retained and recycled as a portion of the superheated vapor used to vaporize newly introduced prepared biomass material. As shown, retained vapor component 208 is routed through heat exchanger 209 to heat it to the desired temperature. The heat source or thermal energy source can include steam, electricity, hot flue gases or any other desired heating source. As shown, hot flue gas is used. The temperature is controlled such that the pressure in the system is maintained at the target and there is adequate energy present to evaporate the desired amount of liquid. The pressure can also be controlled by the flow rate of the superheated vapor stream and the heat input to heat exchanger 209.

Referring to FIG. 2, the remaining portion of vapor component stream 205, represented as numeral 210 is routed to a distillation step. Depending on the distillation configuration, vapor component portion 210 may be condensed before further purification or preferably fed directly into the distillation column as a vapor. The product from the distillation step can further be concentrated using known processes.

Preferably, recovery system 200 operates continuously where prepared biomass material 201 is continuously fed at a desired rate, and vapor component 210 and solid component 206 are continuously removed at a continuous rate. In a preferred embodiment, "fresh" vapor component 208 from one run is retained continuously at a target rate to be used as the superheated vapor stream for the next run. All these rates are adjustable to achieve the desired operating conditions. System fan 214 creates a circulating loop of superheated vapor stream and can be adjusted to obtain the target flow rate.

By using a solventless recovery system according to aspects of the present invention, the points of heat transfer in the system, i.e., addition of heat to the system and heat transfer to the prepared biomass material, take place in the vapor phase in a preferred embodiment, which provides an advantage cause vapor phase heat transfer (convection) is more efficient than solid phase heat transfer (conduction) in the prepared biomass material, which is a bad conductor because it has insulating properties. As mentioned above, in certain embodiments, once steady state is reached no vapor other than that vaporized from the liquid of the prepared biomass material contacts the solid component and gas component of the prepared biomass material in the system, which prevents or reduces dilution that would come from the addition of process steam or other vapor to replenish the superheated vapor stream. The collected gas component can be fed directly to a distillation column for separation of the desired volatile organic compound(s), which can provide significant energy savings. The advantage of this system is that the vapors that contact the wet solids are only those vapors that have been previously removed from the solids so that there is no dilution or explosion risk, etc.

The following examples are presented to further illustrate the invention, but they are not to be construed as limiting the scope of the invention.

Illustrative Embodiments

EXAMPLE A

In this example, various samples of fresh chopped *sorghum* are mixed with a variety of added components as listed in Table A.1 and are stored in silage tubes for 258 days. The amount of ethanol produced in each experiment is shown in the bottom row of the table. The addition rates of the selected additives are shown in Table A.2.

TABLE A.1

| | 2010 Experiments | | | | | | | | |
|---|---|---|---|---|---|---|---|---|---|
| | WITHOUT ACID | WITHOUT ACID | WITHOUT ACID | WITHOUT ACID | WITHOUT ACID | WITH ACID | WITH ACID | WITH ACID | WITH ACID |
| | Experiment # | | | | | | | | |
| | 1 | 2 | 3 | 4 | 5 | 6 | 7 | 8 | 9 |
| Estimated Mass | 20 tonnes | 20 tonnes | 20 tonnes | 20 tonnes | 20 tonnes | 20 tonnes | 20 tonnes | 20 tonnes | 20 tonnes |
| Moisture Content | 68% | 68% | 68% | 68% | 68% | 68% | 68% | 68% | 68% |
| Storage Method | Silage Tube | Silage Tube | Silage Tube | Silage Tube | Silage Tube | Silage Tube | Silage Tube | Silage Tube | Silage Tube |
| Primary Yeast | Ethanol Red | Ethanol Red | Ethanol Red | Ethanol Red | Ethanol Red | Ethanol Red | Ethanol Red | Ethanol Red | Ethanol Red |
| Helper Yeast | | | BioSaf | BioSaf | BioSaf | | | BioSaf | BioSaf |
| Bacterial Inhibitor | Lactrol | Lactrol | Lactrol | Lactrol | Lactrol | Lactrol | Lactrol | Lactrol | Lactrol |
| Cellulose to Glucose | | Cellulase CE-2 | | Cellulase CE-2 | Cellulase CE-2 | | Cellulase CE-2 | Cellulase CE-2 | Cellulase CE-2 |
| Starch to Glucose | | Amylase | | Amylase | Amylase | | Amylase | Amylase | Amylase |
| Other enzyme activities: accessory enzymes | | | | | Liquicell 2500 | | | | Liquicell 2500 |
| Result (gallons Ethanol/initial dry metric tonne) | 36 | 48 | 35 | 35 | 46 | 36 | 45 | 36 | 42 |

TABLE A.2

| ADDITIVE | Rates |
|---|---|
| LACTROL | 1.6 g/wet tonne |
| Ethanol Red | 0.11 kg/wet tonne |
| BioSaf | 0.11 kg/wet tonne |
| Cellulase CE-2 | 0.22 kg/wet tonne |
| Amylase | 0.11 kg/wet tonne |
| Liquicell | 0.11 kg/wet tonne |
| 93% Concentrated Sulfuric Acid | 0.42 L/wet tonne |

The experiments of Example A demonstrated the principle of ethanol production in silage piles and the duration of that storage. Further, they demonstrated effects of certain additive. All cases in the example produced a significant amount of ethanol indicating that embodiments of the invention can be quite robust. In Table A.1, all but the last row describe what additives went into the test. The bottom row describes the result in terms of ethanol production in that experiment. In general, the experiments with acid showed superior stability to those without acid. Nevertheless, experiments without acid still yielded ethanol production, indicating that an acid additive is optional.

EXAMPLE B

In Example B, three additional experiments are shown in Table B.1. The addition rates of the selected additives are shown in Table B.2.

TABLE B.1

| | 2011 Experiments | | |
|---|---|---|---|
| | WITH ACID | WITH ACID | WITH ACID |
| | Experiment # | | |
| | 1 | 2 | 3 |
| Estimated Mass | 450 tonnes | 450 tonnes | 100 tonnes |
| Moisture Content | 76% | 76% | 69% |
| Storage Method | Bunker | Bunker | Silage Tube |
| Yeast | Lallemand Liquid Yeast | Lallemand Liquid Yeast | Lallemand Liquid Yeast |
| Bacterial Inhibitor | Lactrol | Lactrol | Lactrol |
| Cellulose to Glucose | Novozymes Cellic CTec2 | Novozymes Cellic CTec2 | Novozymes Cellic CTec2 |
| Chop Size | 3 mm | 13 mm | 13 mm |
| Result (gallons Ethanol/initial dry ton) | 50 | 51 | 48 |
| Days in Storage | 330 | 330 | 315 |

TABLE B.2

| ADDITIVE | Rates |
|---|---|
| LACTROL | 3.2 g/wet ton |
| Lallemand Stabilized Liquid Yeast | 18 fl oz/wet ton |
| Novozymes Celtic CTec2 | 20 fl oz/wet ton |
| 9.3% Concentrated Sulfuric Acid | 3.8 L/wet ton |

The experiments of Example B also demonstrated the effects of certain additives, as well as the effects of scale. Experiments 1 and 2 of Example B were conducted in the same bunker demonstrating that this fermentation technology is stable and efficient at commercial scale.

EXAMPLE C

In these experiments, the GEA SSD™ is used as the solventless recovery unit. In Table C.1 below, the top section describes certain properties of the prepared biomass material that were fed to the system. The next section describes the condition of the solid component exiting the solvent less recovery system. The third section shows the operating conditions of the solvent less recovery system and the last section gives the recovery rates of the main liquid components: ethanol, acetic acid and water. What is shown here in all cases is the ability to recover >90% of the ethanol that is in the solids (100% in some cases), and the ability to vary the amount of ethanol and water recovery based on the conditions of the solvent less recovery system. Samples 10, 11, and 12 below also contain significant amounts of acetic acid, and show that this process can also be used for the efficient recovery of acetic acid

TABLE C.1

| | Sample 1 | Sample 2 | Sample 3 | Sample 4 | Sample 5 | Sample 6 | Sample 7 | Sample 8 | Sample 9 | Sample 10 | Sample 11 | Sample 12 |
|---|---|---|---|---|---|---|---|---|---|---|---|---|
| Prepared Biomass Composition ("Feed") | | | | | | | | | | | | |
| Liquid in Feed (%) | 80.2% | 79.9% | 82% | 79% | 31% | 82% | 80% | 80% | 58% | 70% | 70% | 70% |
| Water in Liquid (%) | — | 95.1% | 94.9% | 95.0% | 99.9% | 95.7% | 95.8% | 95.8% | 98.6% | 94.6% | 0.946 | 0.946 |
| Ethanol in Liquid (%) | — | 4.2% | 4.4% | 4.5% | 0.0% | 3.9% | 3.8% | 3.8% | 0.6% | 2.8% | 0.028 | 0.028 |
| Acetic Acid in Liquid (%) | — | 0.7% | 0.7% | 0.5% | 0.1% | 0.4% | 0.4% | 0.4% | 0.8% | 2.6% | 2.6% | 2.6% |
| Solid Component | | | | | | | | | | | | |
| Liquid in Solid Component (%) | 66.4% | 58% | 39% | 31% | 7% | 67% | 49% | 38% | 37% | 55% | 46% | 39% |
| Solid Component Temperature (F.) Operating Conditions | 83 | 87 | 89 | 90 | 89 | 86 | 73 | 87 | 82 | 88 | 82 | 91 |
| Vapor Temperature at Inlet (F.) | 349 | 423 | 594 | 428 | 487 | 471 | 426 | 446 | 311 | 297 | 401 | 441 |
| Exhaust Temperature (F.) | 225 | 235 | 295 | 370 | 401 | 275 | 298 | 347 | 307 | 237 | 302 | 351 |
| Operating Pressure (psig) | 3 | 3 | 3 | 40 | 20 | 3 | 2 | 20 | 20 | 3 | 3 | 20 |
| % Removal | | | | | | | | | | | | |
| Ethanol | — | 95% | 99% | 100% | 100% | 96% | 95% | 99% | 100% | 90% | 93% | 98% |
| Acetic Acid | — | 45% | 94% | 98% | 100% | 69% | 24% | 96% | 100% | 82% | 84% | 96% |
| Water | — | 64% | 86% | 92% | 90% | 61% | 76% | 84% | 72% | 46% | 64% | 76% |
| Total Liquids | — | 65% | 87% | 92% | 90% | 63% | 77% | 85% | 72% | 48% | 66% | 77% |

EXAMPLE D

Some of the conditions tested provided sufficient pre-treatment of the biomass coming out of the volatiles recovery unit to allow for conversion of some of the remaining cellulose to biomass. Conditions from Samples 6 and 7 in Example C above produced statistically significant quantities of ethanol when a small amount of enzymes and yeast were added to the sample of the remaining solid component and were stored in an anaerobic environment. Other conditions tested were from Sample 3, 4, 8, 10, and 12. These samples produced no ethanol when placed in the same test conditions as samples 6 and 7. The conclusion from this is that under the test conditions described in sample numbers 6 and 7, certain embodiments of the present invention can be used for the subsequent production of cellulosic ethanol by ensiling the solid component from the volatile organics recovery unit.

EXAMPLE E

In these experiments, a 700 ton pile was prepared according to aspects of the invention and stored in a bunker. On day 504 of storage in the bunker, three samples were taken from the top, center, and bottom of pile, all showed similar levels of compounds. The samples were stored at 4 degrees C.
Sample Prep:
The samples were squeezed through a 60 mL syringe without filtration, and the liquid was collected.
Testing Conditions:
1) The samples were tested with an Agilent 7890 GC with a 5975 C mass spectrometer under the following conditions:
Agilent CTC autosampler with headspace option
2.5 ml heated syringe, 1 ml injection size into S/SL inlet @ 130 C, 20:1 split ratio
Separation on a 60M DB 624 column, 0.25 id with 1.4 µm film The samples were prepared by place 0.25 ml into a 20 ml headspace vial. 1 ml of vapor was injected after equilibration at 60 C for 10 min.
2) The samples were tested with an Agilent 6890 GC with a 5973 Mass Spectrometer under the following conditions:
Perkin Elmer Turbomatrix 40 headspace autosampler
60 M DB5 MS 0.25 mm id, 1.0 µm film 100:1 split ratio
The samples were prepared by place 0.25 ml into a 20 ml headspace vial. Vapor was injected for 20 seconds after equilibration at 90 C for 15 min.
The following compounds were identified in the headspace under both conditions, indicating that these compounds were produced and can be potentially recovered using the solventless recovery system and captured during a subsequent distillation process in certain embodiments.

| | | | |
|---|---|---|---|
| Acetaldehyde | Methanol | Ethanol | Propanol |
| Acetone | Methyl acetate | Acetone | Ethyl formate |
| n-propyl alcohol | ethyl acetate | 2-butanol | 2-methyl-1-propanol |
| 2-propen-1-ol | Acetic acid | 3-methyl-1-butanol | 2-methyl-1-butanol |
| 3-buten-2-ol | | | |

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A method for producing ethanol comprising:
   generating at least about 10 tons of prepared biomass material comprising at least one additive added to a lignocellulosic biomass comprising a sugar, wherein said at least one additive comprises a microbe, an acid, and/or an enzyme;
   storing the prepared biomass material for at least about 24 hours in a storage facility to generate a stored, prepared biomass material having about 2 wt % to about 50 wt % ethanol;
   introducing the stored, prepared biomass material to a pressurized compartment of a recovery system;
   contacting the stored, prepared biomass material with a superheated vapor stream in the pressurized compartment to vaporize at least a portion of the ethanol in the stored, prepared biomass material to provide at least a portion of a vapor component;
   retaining an amount of the vapor component in the recovery system for use as at least part of the superheated vapor stream;
   providing another amount of the vapor component to a distillation unit and releasing from the system at least a portion of the stored, prepared biomass material after vaporization to provide a solid component.

2. The method of claim 1 wherein at least about 700 tons of prepared biomass material is generated in a time period in a range of about 1 to 7 months.

3. The method of claim 2, wherein at least about 25,000 tons of prepared biomass material is generated.

4. The method of claim 3, wherein at least about 100,000 tons of prepared biomass material is generated.

5. The method of claim 4, wherein at least about 1,200,000 tons of prepared biomass is generated.

6. The method of claim 1, wherein about 14-16 gallons of ethanol is recovered per one ton of prepared biomass material.

7. The method of claim 1 wherein the lignocellulosic biomass comprises at least one fermentable sugar producing plant.

8. The method of claim 7 wherein the at least one fermentable sugar producing plant comprises at least one of *sorghum*, sugarcane, sugar beet, energy cane, and any combination thereof.

9. The method of claim 7 wherein the lignocellulosic biomass comprises at least two different plant types, wherein each plant type has a different harvest season.

10. The method of claim 7 wherein the at least one sugar-producing plant is harvested when said plant has reached at least about 80% of its sugar production potential.

11. The method of claim 7, wherein the lignocellulosic biomass comprises a stalk component and a leaf component of the at least one sugar-producing plant.

12. The method of claim 1 wherein the storing step comprises storing the prepared biomass material for a time period in a range of about 72 hours to about 700 days.

13. The method of claim 1 wherein the storing step comprises storing the prepared biomass material for a time period sufficient to allow a conversion efficiency of sugar to at least one volatile organic compound of at least about 95%.

14. The method of claim 1 wherein the storage facility is located about 0.5 mile from the recovery system.

15. The method of claim 1 wherein the storing step further comprises forming at least one pile of prepared biomass material having a height of at least about 10 feet.

16. The method of claim 15 wherein the forming of the at least one pile further comprises compacting at least a portion of the prepared biomass material to facilitate establishing of an anaerobic environment.

17. The method of claim 1, wherein the solid component contains liquid in a range of about 30 wt % to about 70 wt %.

18. The method of claim 1, wherein the superheated vapor stream contains ethanol in a range of about 1 wt % and about 50 wt %.

19. The method of claim 1, wherein the solid component exiting the recovery system has a temperature of less than about 50° C.

20. The method of claim 1 further comprising operating the recovery system at a pressure in a range of 3 psig to about 60 psig.

21. The method of claim 1 further comprising removing in a range of 50% to 95% of the ethanol in the stored prepared biomass material.

22. The method of claim 1 further comprising removing in a range of 50% to 90% of the ethanol in the stored prepared biomass material.

23. The method of claim 1 further comprising: operating the recovery system at steady state where the superheated vapor stream consists essentially of the vapor component.

24. The method of claim 1 wherein the superheated vapor stream comprises about 4 wt % to 15 wt % ethanol.

25. A method for processing producing a storable wet biomass containing ethanol, said method comprising:
   adding at least one additive to at least about 10 tons of a solid lignocellulosic biomass to generate a prepared biomass material, said solid lignocellulosic biomass comprising a sugar-producing plant, wherein said at least one additive comprises a microbe, an acid, and/or an enzyme;
   allowing conversion of at least a portion of the sugar in the prepared biomass material into ethanol to produce a stored, prepared biomass material, wherein said stored, prepared biomass material comprises about 2 wt % to about 50 wt % ethanol; wherein the prepared biomass material is capable of being stored for up to about 700 days without significant degradation of the ethanol;
   introducing the stored, prepared biomass material comprising the ethanol to a recovery system to separate the stored, prepared biomass material into at least a vapor component comprising ethanol and a solid component;
   contacting the stored, prepared biomass material with a superheated vapor stream in a pressurized compartment of the recovery system to vaporize at least a portion of the ethanol in the stored, prepared biomass material to provide at least a portion of a vapor component;
   retaining at least a portion an amount of the vapor component in the recovery system for use as at least part of the superheated vapor stream; and
   releasing from the system at least a portion of the stored, prepared biomass material after vaporization to provide the solid component.

26. A method comprising:
   providing at least 10 tons of a stored prepared biomass material to a recovery system, wherein the stored, prepared biomass material comprises in a range of 2 wt % to 50 wt % ethanol; and wherein the stored, prepared biomass material is generated by adding at least one of a microbe and an acid to a lignocellulosic biomass to generate a prepared biomass material and storing the prepared biomass material for at least 24 hours;

contacting the stored, prepared biomass material with a superheated vapor stream in a compartment of the recovery system to vaporize at least a portion of the ethanol provide at least a portion of the vapor component;

retaining an amount of the vapor component in the recovery system for use as at least part of the superheated vapor stream; and releasing from the compartment at least a portion of the stored, prepared biomass material after vaporization to provide a solid component.

27. The method of claim 26 wherein the lignocellulosic biomass comprises at least one fermentable sugar producing plant.

28. The method of claim 27 wherein the at least one fermentable sugar producing plant comprises at least one of *sorghum*, sugarcane, sugar beet, energy cane, and any combination thereof.

29. The method of claim 26 further comprising operating the recovery system to vaporize 50% to 95% of the ethanol in the stored prepared biomass material and to produce a vapor component comprising about 1 wt % to 50 wt % ethanol and a solid component comprising liquid in a range of about 30 wt % to about 70 wt %.

30. The method of claim 26 wherein the superheated vapor stream comprises about 1 wt % to 50 wt % ethanol.

31. The method of claim 26, wherein the solid component exiting the recovery system has a temperature of less than about 50° C.

32. The method of claim 26 further comprising operating the recovery system at a pressure in a range of 3 psig to about 60 psig.

33. The method of claim 26 wherein the retaining of an amount of vapor component produces a superheated vapor stream that consists essentially of the vapor component.

34. The method of claim 26 wherein the superheated vapor stream comprises about 4 wt % to 15 wt % ethanol.

35. The method of claim 26 further comprising providing an amount of the vapor component to a distillation unit to generate an overhead product stream comprising ethanol.

* * * * *